(12) United States Patent
Corringham et al.

(10) Patent No.: US 8,865,710 B2
(45) Date of Patent: *Oct. 21, 2014

(54) METHODS OF TREATING PROLIFERATIVE DISEASES

(75) Inventors: Robert E. Corringham, San Diego, CA (US); Patrick B. O'Donnell, San Diego, CA (US); Joyce K. James, San Diego, CA (US)

(73) Assignee: Ambit Biosciences Corporation, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/320,217

(22) PCT Filed: May 14, 2010

(86) PCT No.: PCT/US2010/034926
§ 371 (c)(1),
(2), (4) Date: Jun. 21, 2012

(87) PCT Pub. No.: WO2010/132787
PCT Pub. Date: Nov. 18, 2010

(65) Prior Publication Data
US 2012/0258081 A1    Oct. 11, 2012

Related U.S. Application Data

(60) Provisional application No. 61/178,472, filed on May 14, 2009, provisional application No. 61/243,977, filed on Sep. 18, 2009.

(51) Int. Cl.
| | | |
|---|---|---|
| *A61K 31/5377* | (2006.01) | |
| *A61K 31/429* | (2006.01) | |
| *A61K 9/48* | (2006.01) | |
| *A61K 9/16* | (2006.01) | |
| *A61K 9/08* | (2006.01) | |
| *A61K 9/14* | (2006.01) | |

(52) U.S. Cl.
CPC ............ *A61K 31/429* (2013.01); *A61K 9/4866* (2013.01); *A61K 9/1641* (2013.01); *A61K 9/08* (2013.01); *A61K 9/145* (2013.01)
USPC ..................................................... 514/233.2

(58) Field of Classification Search
USPC ...................................................... 514/233.2
See application file for complete search history.

(56) References Cited

U.S. PATENT DOCUMENTS

| | | | |
|---|---|---|---|
| 4,328,245 A | 5/1982 | Yu | |
| 4,409,239 A | 10/1983 | Yu | |
| 4,410,545 A | 10/1983 | Yu | |
| 7,820,657 B2 | 10/2010 | Bhagwat | |
| 7,968,543 B2 * | 6/2011 | James et al. | 514/231.5 |
| 2009/0131426 A1 | 5/2009 | Bhagwat | |
| 2010/0292177 A1 | 11/2010 | Armstrong | |
| 2012/0070410 A1 * | 3/2012 | Apuy et al. | 424/85.4 |

FOREIGN PATENT DOCUMENTS

| | | | |
|---|---|---|---|
| WO | WO 2007/109120 | * | 9/2007 |
| WO | WO 2011/056939 | | 5/2011 |

OTHER PUBLICATIONS

Cheson et al., "Revised Recommendations of the International Working Group for Diagnosis, Standardization of Response Criteria, Treatment Outcomes, and Reporting Standards for Therapeutic Trials in Acute Myeloid Leukemia," J. Clin. Oncol. 21(24):4642-4649 (2003).
Cortes et al., "Phase 1 AML Study of AC220, a Potent and Selective Second Generation FLT3 Receptor Tyrosine Kinase Inhibitor," Blood 112(11):284-285 (2008).
Cortes et al., "Human pharmacokinetics of AC220, a potent and selective class III receptor tyrosine kinase inhibitor," Blood 110(11):477A (2007).
Frohling et al., "Prognostic Significance of Activating FLT3 Mutations in Younger Adults (16 to 60 years) With Acute Myeloid Leukemia and Normal Cytogenetics: A Study of the AML Study Group Ulm," Blood 100:4372-4380 (2002).
Gilliland et al., "The Roles of FL T3 in Hematopoiesis and Leukemia," Blood 100(5): 1532-1542 (2002).
James et al., "Clinical Pharmacokinetics and FLT3 Phosphorylation of AC220, a Highly Potent and Selective Inhibitor of FLT3," Blood 112(11):912, Abstract 2637 (2008).
Kelly et al., "CT53518, A Novel Selective FLT3 Antagonist for the Treatment of Acute Myelogenous Leukemia (AML)," Cancer Cell 1:421-432 (2002).
Levis et al., "A FLT3-Targeted Tyrosine Kinase Inhibitor Is Cytotoxic to Leukemia Cells In Vitro and In Vivo," Blood 99(11):3885-3891 (2002).
Levis et al., "FLT3 Tyrosine Kinase Inhibitors," Int. J. Hematol. 82:100-107 (2005).
Stirewalt et al., "The Role of FLT3 in Haematopoietic Malignancies," Nat. Rev. Cancer 3:650-665 (2003).
Therasse et al., "New Guidelines to Evaluate the Response to Treatment in Solid Tumors," Journal of the National Cancer Institute 92(3): 205-216 (2000).
Vardiman et al., "The World Health Organization (WHO) Classification of the Myeloid Neoplasms" Blood 100(7):2293-2302 (2002).
Weisberg et al., "Inhibition of Mutant FL T3 Receptors in Leukemia Cells by the Small Molecule Tyrosine Kinase Inhibitor PKC412," Cancer Cell 1:433-443 (2002).
Yamamoto et al., "Activating Mutation of D835 Within the Activation Loop of FLT3 in Human Hematologic Malignancies," Blood 97(8):2434-2439 (2001).
Yee et al., "SU5416 and SU5614 Inhibit Kinase Activity of Wild-Type and Mutant FLT3 Receptor Tyrosine Kinase," Blood 100(8):2941-2949 (2002).

* cited by examiner

*Primary Examiner* — Samantha Shterengarts
(74) *Attorney, Agent, or Firm* — Jones Day

(57) ABSTRACT

Provided herein are methods of administering N-(5-tert-butyl-isoxazol-3-yl)-N'-{4-[7-(2-morpholin-4-yl-ethoxy)imidazo[2,1-b][1,3]benzothiazol-2-yl]phenyl}urea, or a pharmaceutically acceptable salt or solvate thereof, to human patients, including a specific patient population. Specifically, dosing, dosing schedules or dosing regimens are provided herein. Methods of treating proliferative diseases or FLT-3 mediated diseases in humans are also provided.

6 Claims, 4 Drawing Sheets

METHODS OF TREATING PROLIFERATIVE DISEASES

CROSS REFERENCE TO RELATED APPLICATIONS

This application is a National stage under 35 U.S.C. 371(c) of International Application No. PCT/US2010/034926 filed May 14, 2010, which claims the benefit of the priority of U.S. Provisional Application No. 61/178,472, filed May 14, 2009, and U.S. Provisional Application No. 61/243,977, filed Sep. 18, 2009, the disclosures of which are incorporated herein by reference in their entireties.

FIELD

Provided herein are methods of administering N-(5-tert-butyl-isoxazol-3-yl)-N'-{4-[7-(2-morpholin-4-yl-ethoxy)imidazo[2,1-b][1,3]benzothiazol-2-yl]phenyl}urea, or a pharmaceutically acceptable salt or solvate thereof, to human patients, including methods of administration to a specific patient population in order to treat or manage certain diseases. Also provided are dosing, dosing schedules or dosing regimens. Methods of treating proliferative diseases or FLT-3 mediated diseases in humans, including a specific patient population are also provided.

BACKGROUND

Fms-like tyrosine kinase 3 (FLT3), which is also known as FLK-2 (fetal liver kinase 2) and STK-1 (stem cell kinase 1), plays an important role in the proliferation and differentiation of hematopoietic stem cells. FLT3 receptor kinase is expressed in normal hematopoietic cells, placenta, gonads, and brain. However, this enzyme is expressed in acute myeloid leukemia cells in approximately 90% of acute myeloid leukemia (AML) patients and in acute lymphoblastic leukemia cells in a fraction of acute lymphoblastic leukemia (ALL) patients. This enzyme can also be found on cells from patients with chronic myeloid leukemia in lymphoid blast crisis.

It has been reported that FLT3 kinase is mutated in 30% of acute myeloid leukemia (AML) and in a subset of acute lymphoblastic leukemia (ALL) as well (Gilliland et al., *Blood* 2002, 100, 1532-1542; Stirewalt et al., *Nat. Rev. Cancer* 2003, 3, 650-665). The most common activating mutations in FLT3 are internal tandem duplications (ITD) found within the juxtamembrane region. The FLT3 ITD mutation has been associated with poor prognosis (Frohling et al., *Blood* 2002, 100, 4372-4380). The second most frequent activating mutation of FLT3 is the missense mutation in the tyrosine kinase domain, mainly at D835 within the activation loop of the tyrosine kinase domain (Yamamoto et al., *Blood* 2001, 97, 2434-2439). In addition, many non-mutated FLT3 patients show evidence of FLT3 activation. The association of FLT3 mutations with poor clinical outcome and the therapeutic effects observed in early stage clinical trials with first generation FLT3 inhibitors strongly implicate FLT3 as an important target for small molecule intervention in AML.

More than a dozen known FLT3 inhibitors are being developed and some have shown promising clinical effects against AML (Levis et al. *Int. J. Hematol.* 2005, 82, 100-107). It has been reported that some of small-molecule FLT3 inhibitors are effective in inducing apoptosis in cell lines with FLT3-activating mutations and prolonging survival of mice that express mutated FLT3 in their bone marrow cells (Levis et al., *Blood* 2002, 99, 3885-3891; Kelly et al., *Cancer Cell* 2002, 1, 421-432; Weisberg et al., *Cancer Cell* 2002, 1, 433-443; Yee et al., *Blood* 2002, 100, 2941-2949).

Despite the success in identification of small molecules that inhibit protein tyrosine kinases, there continues to be an effective method of using or administering such compounds, particularly to humans having AML and ALL, including compounds useful for the treatment of FLT-3 mediated diseases. Methods with improved therapeutic index, i.e, where adverse or unwanted effects of therapy are reduced while efficacy is maintained, are sought.

SUMMARY OF THE DISCLOSURE

In certain embodiments, provided herein is a method of treating acute myeloid leukemia in a patient, which comprises administering to a patient having acute myeloid leukemia a therapeutically effective amount of the compound of Formula I:

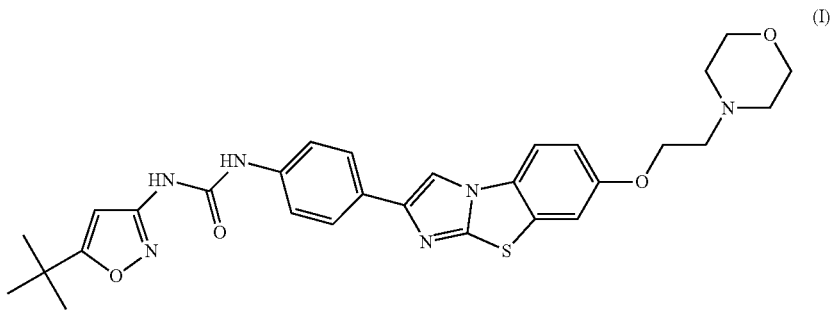 [SMILES: CC(C)(C)c1cc(NC(=O)Nc2ccc(-c3cn4c(n3)sc3cc(OCCN5CCOCC5)ccc34)cc2)no1]

or a pharmaceutically acceptable salt or solvate thereof, wherein the patient is relapsed or refractory to a prior cancer therapy. In certain embodiments, the patient is relapsed after a first line cancer therapy or a second line cancer therapy.

In certain embodiments, the patient is 60 years or older and relapsed after a first line cancer therapy. In certain embodiments, the patient is 18 years or older and is relapsed or refractory after a second line cancer therapy. In certain embodiments, the patient is 60 years or older and is primary refractory to a first line cancer therapy. In certain embodiments, the patient is 70 years or older and is previously untreated. In certain embodiments, the patient is 70 years or older and is ineligible and/or unlikely to benefit from cancer therapy.

In certain embodiments, the patients previously untreated who are ineligible and/or unlikely to benefit from cancer therapy include patients having at least one of the following adverse factors: prior MDS (myelodysplastic syndrome), unfavorable cytogenetics at diagnosis, ECOG (Eastern Cooperative Oncology Group) performance status of 2, or ≥75 years of age.

In certain embodiments, the therapeutically effective amount used in the methods provided herein is at least 12 mg per day. In certain embodiments, the therapeutically effective amount is 12, 50, 90, 100, 135, 150, 200, 250, 300, 350, 400, 450 mg per day or more. In certain embodiments, the compound is administered continuously.

In certain embodiments, provided herein is a method for treating proliferative diseases by administering to a mammal having a proliferative disease at least 12 mg per day of a compound of Formula I or a pharmaceutically acceptable salt or solvate thereof, and wherein the compound is administered on an empty stomach.

In certain embodiments, the proliferative disease in the methods provided herein is cancer. In certain embodiments, the proliferative disease in the methods provided herein is a solid tumor. In yet another embodiment, the proliferative disease in the methods provided herein is a blood-borne tumor. In yet another embodiment, the proliferative disease is leukemia. In certain embodiments, the leukemia is acute myeloid leukemia. In certain embodiments, the leukemia is acute lymphocytic leukemia. In still another embodiment, the leukemia is a refractory or drug resistant leukemia.

In certain embodiments, the drug resistant leukemia is drug resistant acute myeloid leukemia. In certain embodiments, the mammal having the drug resistant acute myeloid leukemia has an activating FLT3 mutation. In still another embodiment, the drug resistant acute myeloid leukemia has a FLT3 internal tandem duplication (ITD) mutation.

Each method provided herein may further comprise administering a second therapeutic agent. In certain embodiments, the second therapeutic agent is an anticancer agent. In certain embodiments, the second therapeutic agent is a protein kinase inhibitor; In certain embodiments, a tyrosine kinase inhibitor; and in yet another embodiment, a second FLT3 kinase inhibitor.

DETAILED DESCRIPTION

Figure 1:
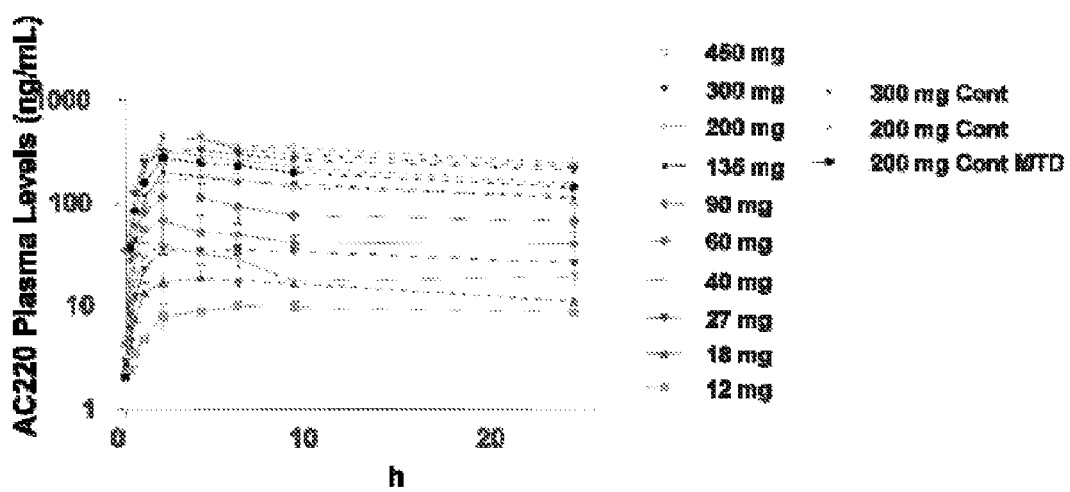
FIG. 1 depicts the plasma concentrations of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt over time in human dosed at 12, 18, 27, 40, 60, 90, 135, 200, 300 and 450 mg.

To facilitate understanding of the disclosure set forth herein, a number of terms are defined below.

The term "remission" refers to where a subject has abatement or lessening of the severity of disease or its symptoms.

The term "complete remission" or CR as it refers to leukemia means a subject has achieved one or more of the following criteria: 1) a morphologic leukemia-free state with no evidence of extramedullary leukemia 2) an absolute neutrophil count (ANC) of more than $1 \times 10^9/L$ and platelet count of more than $100 \times 10^9/L$ 3) normal marrow differential with less than 5% blasts and 4) independence from red blood cell (RBC) and platelet transfusions. In certain embodiments, a subject in CR has achieved criterion 1, or criteria 1 and 3, or criteria 1, 2, and 3. In certain embodiments, a subject in CR has achieved criterion 1, or criteria 1 and 3, or criteria 1, 2, 3 and 4. See, e.g., the recommendations of the International Working Group in 2003 (Cheson et al. *J. Clin. Oncol.* 2003 21(24): 4642-4649). The definition of "complete remission" is expected to evolve as newer and more sensitive technologies are developed to measure leukemic burden. Other categories of patients who fulfill the morphologic criteria for complete remission are as follows: "complete remission with incomplete platelet recovery (CRp)" where a subject fulfills all of the criteria for CR except for the platelet count, which is less than $100 \times 10^9/L$ and "complete remission with incomplete hematological recovery (CRi), where a subject fulfills all of the criteria for CR except for the neutrophil count, which is less than $1 \times 10^9/L$. "Partial remission" or "PR" is used to describe the condition where a subject has achieved the hematological values for a CR and a decrease of least 50% in the percentage of blasts in the bone marrow aspirate to 5% to 25%.

The terms "FLT3-mediated diseases or disorders" shall include diseases associated with or implicating FLT3 activity, for example, the overactivity of FLT3, and conditions that accompany with these diseases. The term "overactivity of FLT3" refers to either 1) FLT3 expression in cells which normally do not express FLT3; 2) FLT3 expression by cells which normally do not express FLT3; 3) increased FLT3 expression leading to unwanted cell proliferation; or 4) mutations leading to constitutive activation of FLT3. Examples of "FLT3-mediated diseases or disorders" include disorders resulting from over stimulation of FLT3 or from abnormally high amount of FLT3 activity, due to abnormally high amount of FLT3 or mutations in FLT3. It is known that overactivity of FLT3 has been implicated in the pathogenesis of a number of diseases, including inflammatory and autoimmune diseases, cell proliferative disorders, neoplastic disorders and cancers as described herein.

The term "FLT3-ITD allelic ratio" refers to the percentage of tumor DNA alleles harboring the FLT3-ITD mutation normalized to the percent blast cells in a patient sample. In one embodiment, a low FLT3-ITD allelic ratio is where less than 25% of normalized tumor DNA alleles is a FLT3-ITD allele. In certain embodiments, an intermediate FLT3-ITD allelic ratio is where between 25% and 50% of normalized tumor DNA alleles is a FLT3-ITD allele. In certain embodiments, a high FLT3-ITD allelic ratio is where greater than 50% of normalized tumor DNA alleles is a FLT3-ITD allele.

The term "proliferative disorder or disease" refers to unwanted cell proliferation of one or more subset of cells in a multicellular organism resulting in harm (i.e., discomfort or decreased life expectancy) to the multicellular organisms. A proliferative disorder or disease can occur in different types of animals and humans. For example, as used herein, "proliferative disorder or disease" includes neoplastic disorders and other proliferative disorders.

The term "neoplastic disorder or disease" or "cancer" refers to a tumor resulting from abnormal or uncontrolled cellular growth. Examples of neoplastic disorders include, but are not limited to, hematopoietic disorders, such as the myeloproliferative disorders, thrombocythemia, essential thrombocytosis (ET), angiogenic myeloid metaplasia, myelofibrosis (MF), myelofibrosis with myeloid metaplasia (MMM), chronic idiopathic myelofibrosis (IMF), polycythemia vera (PV), the cytopenias, and pre-malignant myelodysplastic syndromes; cancers, such as glioma cancers, lung cancers, breast cancers, colorectal cancers, prostate cancers, gastric cancers, esophageal cancers, colon cancers, pancreatic cancers, ovarian cancers, or hematologic malignancies. In certain embodiments, the tumor is germ cell tumor, melanoma gastrointestinal stromal tumor (GIST), mast cell tumor, melanoma, or neuroblastoma.

The term hematopoietic stem cell transplantation, or HSCT, refers to the transplantation of hematopoietic progenitor cells into a patient. The hematopoietic progenitor cells may be obtained from bone marrow, peripheral blood, or from umbilical cord blood. In certain embodiments, the hematopoietic stem cell transplantation is allogeneic, syngeneic or autologous. In certain embodiments, the hematopoietic stem cell transplantation is allogeneic.

The term "hematologic malignancy" refers to cancer of the body's blood-forming and immune system—the bone marrow and lymphatic tissue. Examples of hematological malignancies include, for instance, myelodysplasia, myelodysplastic syndrome (MDS), myeloproliferative disorder (MPD) (which includes polycythemia vera (PV or PCV), essential thrombocytosis (ET) and myelofibrosis), amyloid neuropathy, lymphoma (non-Hodgkin's lymphoma), Hodgkin's disease (also called Hodgkin's lymphoma), multiple myeloma (MM) and its variants, and leukemia such as acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS) and mixed lineage leukemia (MLL).

The term "leukemia" refers to malignant neoplasms of the blood-forming tissues, including, but not limited to, chronic lymphocytic leukemia, chronic myeloid leukemia, chronic myelocytic leukemia, acute lymphoblastic leukemia, acute myeloid leukemia and acute myeloblastic leukemia. The leukemia can be relapsed, refractory, or resistant to conventional therapy.

The term "promyelocytic leukemia" or "acute promyelocytic leukemia" refers to a malignancy of the bone marrow in which there is a deficiency of mature blood cells in the myeloid line of cells and an excess of immature cells called promyelocytes. It is usually marked by an exchange of parts of chromosomes 15 and 17.

The term "acute lymphocytic leukemia," "acute lymphoblastic leukemia," or "ALL" refers to a malignant disease caused by the abnormal growth and development of early nongranular white blood cell or lymphocytes.

The term "T-cell leukemia" refers to a disease in which certain cells of the lymphoid system called T lymphocytes or T cells are malignant. T cells are white blood cells that normally can attack virus-infected cells, foreign cells, and cancer cells; and produce substances that regulate the immune response.

The term MDS, or myelodysplastic syndromes, refers to a diverse set of hematological disorders characterized by the presence of at least one of the following in the bone marrow: blast cells, cytogenetic abnormalities or morphologic abnormalities (dysplasia). In one embodiment, MDS includes the five subtypes defined by the French-American-British Work Group, such as refractory anemia (RA), refractory anemia with ringed sideroblasts (RARS), refractory anemia with excess blasts (RAEB), refractory anemia with excess blasts in transformation (RAEB-T) and chronic myelomonocytic leukemia (CMML). In another embodiment, MDS includes the subtypes defined by the World Health Organization (WHO) described in Vardiman et al. *Blood* 2002 100(7):2293-2302.

The term "relapsed" refers to where a subject has a recurrence of disease or its manifestations after an improvement or being in complete remission. Relapse after CR, as defined by the International Working Group in 2003 is the reappearance of leukemic blasts in the peripheral blood or ≥5% blasts in the bone marrow aspirate not attributable to any other cause or reappearance or new appearance of extramedullary leukemia. Molecular and/or genetic relapse is characterized by reappearance of a cytogenetic or molecular abnormality. Relapse after PR is similarly defined as the reappearance of significant numbers of peripheral blasts and an increase in percentage of blasts in the bone marrow aspirate to >25% not attributable to any other cause or reappearance or new appearance of extramedullary leukemia.

The term "first line cancer therapy" refers to therapy administered to a subject as an initial regimen to reduce the number of cancer cells. First line therapy is also referred to as induction therapy, primary therapy and primary treatment. Commonly administered first-line therapy for AML is cytarabine-based therapy in which cytarabine is administered often in combination with one or more agents selected from daunorubicin, idarubicin, doxorubicin, mitoxantrone, tipifarnib, thioguanine or gemtuzumab ozogamicin. Common regimens used in cytarabine-based therapy include the "7+3" or "5+2" therapy comprising administration of cytarabine with an anthracycline such as daunorubicin or idarubicin. Another first-line therapy is clofarabine-based therapy in which clofarabine is administered, often in combination with an anthracycline such as daunorubicin, idarubicin or doxorubicin. Other first-line therapy for AML are etoposide-based therapy in which etoposide is administered, often in combination with mitoxantrone, and optionally, with cytarabine. Another first-line therapy for AML (for subtype M3, also called acute promyelocytic leukemia) is all-trans-retinoic acid (ATRA). It is recognized that what is considered "first line therapy" by those of ordinary skill in the art will continue to evolve as new anti-cancer agents are developed and tested in the clinics. A summary of the currently accepted approaches to first line treatment is described in NCCN Clinical Practice Guidelines in Oncology for acute myeloid leukemia and the NCI guidelines on acute myeloid leukemia treatment (see, e.g., http://www.cancer.gov/cancertopics/pdq/treatment/adultAML/HealthProfessional/page7).

The term "second line cancer therapy" refers to a cancer treatment that is administered to a subject who does not respond to first line therapy, that is, often first line therapy is administered or who has a recurrence of cancer after being in remission. In certain embodiments, second line therapy that may be administered includes a repeat of the initial successful cancer therapy, which may be any of the treatments described under "first line cancer therapy". In certain embodiments, second line therapy is the administration of gemtuzumab ozogamicin. In certain embodiments, investigational drugs may also be administered as second line therapy in a clinical trial setting. A summary of the currently accepted approaches to second line treatment is described in the NCCN Clinical Practice Guidelines in Oncology for acute myeloid leukemia and the NCI guidelines on acute myeloid leukemia treatment (see, e.g., http://www.cancer.gov/cancertopics/pdq/treatment/adultAML/HealthProfessional/page5).

The term "refractory" refers to wherein a subject fails to respond or is otherwise resistant to cancer therapy or treatment. The cancer therapy may be first-line, second-line or any subsequently administered treatment. In certain embodiments, refractory refers to a condition where a subject fails to achieve complete remission after two induction attempts. A subject may be refractory due to a cancer cell's intrinsic resistance to a particular therapy, or the subject may be refractory due to an acquired resistance that develops during the course of a particular therapy.

The term "primary refractory" refers to a condition where a subject does not respond to first line cancer therapy.

The term "anticancer agent" is meant to include anti-proliferative agents and chemotherapeutic agents, including, but not limited to, antimetabolites (e.g., 5-fluoro uracil, methotrexate, fludarabine, cytarabine (also known as cytosine arabinoside or Ara-C), including HDAC (high dose cytarabine), gemcitabine, azacytidine, clofarabine, fludarabine and troxacitabine), antimicrotubule agents (e.g., vinca alkaloids, such as vincristine and vinblastine; and taxanes, such as paclitaxel and docetaxel), alkylating agents (e.g., mechlorethamine, chlorambucil, cyclophosphamide, melphalan, melphalan, ifosfamide, carmustine, azacitidine, decitibine, busulfan, cyclophosphamide, dacarbazine, ifosfamide, and nitrosoureas, such as carmustine, lomustine, bischloroethylnitrosourea, and hydroxyurea), platinum agents (e.g., cisplatin, carboplatin, oxaliplatin, satraplatin (JM-216), and CI-973), anthracyclines (e.g., doxorubicin and daunorubicin), antitumor antibiotics (e.g., mitomycin, bleomycin, idarubicin, adriamycin, daunomycin (also known as daunorubicin, rubidomycin, or cerubidine), doxorubicin, mitoxantrone and pixantrone), topoisomerase inhibitors (e.g., etoposide and camptothecins), purine anatagonists, pyrimidine antagonists and nucleoside analogs (e.g., 6-mercaptopurine, 5-fluorouracil, cytarabine, clofarabine, and gemcitabine), cell maturing agents (e.g., arsenic trioxide and tretinoin), DNA repair enzyme inhibitors (e.g., podophyllotoxines, etoposide, irinotecan, topotecan, and teniposide), enzymes that prevent cell survival (e.g., asparaginase and pegaspargase), histone deacetylase inhibitors (e.g., vorinostat), any other cytotoxic agents (e.g., estramustine phosphate, dexamethasone, prednimustine, and procarbazine), hormones (e.g., dexamethasone, prednisone, methylprednisolone, tamoxifen, leuprolide, flutamide, and megestrol), monoclonal antibodies (e.g., gemtuzumab ozogamicin, alemtuzumab, rituximab, and yttrium-90-ibritumomab tiuxetan), immunomodulators (e.g., thalidomide and lenalidomide), Bcr-Abl kinase inhibitors (e.g., AP23464, AZD0530, CGP76030, PD180970, SKI-606, imatinib, BMS354825 (dasatinib), AMN107 (nilotinib), and VX-680), hormone agonists or antagonists, partial agonists or partial antagonists, kinase inhibitors (e.g., sorafenib, imatinib, sunitinib and other yet unmarketed kinase inhibitors), surgery, radiotherapy (e.g., gamma-radiation, neutron bean radiotherapy, electron beam radiotherapy, proton therapy, brachytherapy, and systemic radioactive isotopes), endocrine therapy, biological response modifiers (e.g., interferons, interleukins, and tumor necrosis factor), hyperthemia and cryotherapy, and agents to attenuate any adverse effects (e.g., antiemetics).

The term "subject" refers to an animal, including, but not limited to, a mammal, including a primate (e.g., human), cow, sheep, goat, horse, dog, cat, rabbit, rat, or mouse. The terms "subject" and "patient" are used interchangeably herein in reference, for example, to a mammalian subject, such as a human subject.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "managing" refers to preventing or reducing or avoiding worsening of disease or symptoms of disease.

The terms "prevent," "preventing," and "prevention" are meant to include a method of delaying and/or precluding the onset of a disorder, disease, or condition, and/or its attendant symptoms; barring a subject from acquiring a disease; or reducing a subject's risk of acquiring a disorder, disease, or condition.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. In certain embodiments, each component is "pharmaceutically acceptable" in the sense of being compatible with the other ingredients of a pharmaceutical formulation, and suitable for use in contact with the tissue or gan of humans and animals without excessive toxicity, irritation, allergic response, immunogenicity, or other problems or complications, commensurate with a reasonable benefit/risk ratio. See, *Remington: The Science and Practice of Pharmacy,* 21st Edition; Lippincott Williams & Wilkins: Philadelphia, Pa., 2005; *Handbook of Pharmaceutical Excipients,* 5th Edition; Rowe et al., Eds., The Pharmaceutical Press and the American Pharmaceutical Association: 2005; and *Handbook of Pharmaceutical Additives,* 3rd Edition; Ash and Ash Eds., Gower Publishing Company: 2007; *Pharmaceutical Preformulation and Formulation*, Gibson Ed., CRC Press LLC: Boca Raton, Fla., 2004).

The term "drug resistance" refers to the condition when a disease does not respond to the treatment of a drug or drugs. Drug resistance can be either intrinsic, which means the disease has never been responsive to the drug or drugs, or it can be acquired, which means the disease ceases responding to a drug or drugs that the disease had previously responded to. In certain embodiments, drug resistance is intrinsic. In certain embodiments, the drug resistance is acquired. As used herein, the term "drug resistance" is meant to include imatinib-resistance, dasatinib-resistance, and/or nilotinib-resistance.

The term "hydrate" means a compound provided herein or a salt thereof, which further includes a stoichiometric or non-stoichiometric amount of water bound by non-covalent intermolecular forces.

The term "solvate" means a solvate formed from the association of one or more solvent molecules to a compound provided herein. The term "solvate" includes hydrates (e.g., mono-hydrate, dihydrate, trihydrate, tetrahydrate and the like).

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The Compound

The compound suitable for use in the methods provided herein is N-(5-tert-butyl-isoxazol-3-yl)-N'-{4-[7-(2-morpholin-4-yl-ethoxy)imidazo[2,1-b][1,3]benzothiazol-2-yl]phenyl}urea, having the structure of Formula I:

In yet another embodiment, the compound used in the methods provided herein is a pharmaceutically acceptable salt of the compound of Formula I, which includes, but is not limited to, acetate, adipate, alginate, aspartate, benzoate, benzenesulfonate (besylate), bisulfate, butyrate, citrate, camphorate, camphorsulfonate, cyclopentanepropionate, digluconate, dodecylsulfate, 1,2-ethanedisulfonate (edisylate), ethanesulfonate (esylate), formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate (mesylate), 2-naphthalenesulfonate (napsylate), nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate, or undecanoate salts.

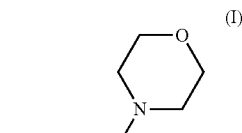

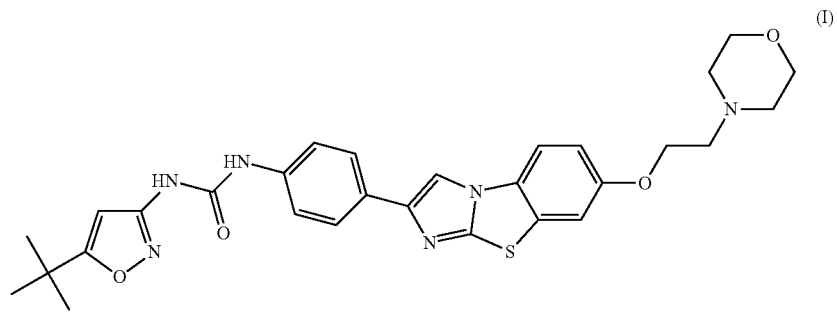 [SMILES: CC(C)(C)c1cc(NC(=O)Nc2ccc(-c3cn4c(n3)sc3cc(OCCN5CCOCC5)ccc34)cc2)no1]

(I)

or a pharmaceutically acceptable salt or solvate thereof. In certain embodiment, the compound is dihydrochloride salt of N-(5-tert-butyl-isoxazol-3-yl)-N'-{4-[7-(2-morpholin-4-yl-ethoxy)imidazo[2,1-b][1,3]benzothiazol-2-yl]phenyl}urea, also known as AC220.

The compound of Formula I or a pharmaceutically acceptable salt or solvate thereof can be prepared according to the methods described in U.S. patent application Ser. No. 11/724,992, filed Mar. 16, 2007, published as U.S. Pub. No. 2007/0232604 on Oct. 4, 2007, and U.S. 61/258,550, filed Nov. 5, 2009, the entireties of which are incorporated by reference herein. The compound can be also synthesized according to other methods apparent to those of skill in the art based upon the teaching herein.

In certain embodiments, the compound used in the methods provided herein is a free base of the compound of Formula I, or a pharmaceutically acceptable solvate thereof. In certain embodiments, the free base is a solid. In certain embodiments, the free base is a solid in an amorphous form. In yet another embodiment, the free base is a solid in a crystalline form. The compound of Formula I in solid forms can be prepared according to the methods described in U.S. patent application Ser. No. 12/233,906, filed Sep. 19, 2008, published as U.S. Pub. No. 2009/0131426 on May 21, 2009, the entirety of which is incorporated by reference herein; or using other methods known in the art.

In certain embodiments, the free base is a pharmaceutically acceptable solvate. In certain embodiments, the free base is a hydrate. In certain embodiments, the pharmaceutically acceptable solvent is a methanol solvate. The methanol solvate of the compound of Formula I can be prepared according to the method described in U.S. patent application Ser. No. 12/233,906, filed Sep. 19, 2008, published as U.S. Pub. No. 2009/0131426 on May 21, 2009, or using other methods known in the art.

In certain embodiments, the pharmaceutically acceptable salt is a hydrochloride, hydrobromide, sulfate, mesylate, esylate, edisylate, besylate, tosylate, or napsylate salt of the compound of Formula I. In certain embodiments, the pharmaceutically acceptable salt is a hydrochloride salt of the compound of Formula I. In certain embodiments, the pharmaceutically acceptable salt is a dihydrochloride salt of the compound of Formula I. In yet another embodiment, the pharmaceutically acceptable salt is a hydrobromide of the compound of Formula I. In yet another embodiment, the pharmaceutically acceptable salt is a sulfate of the compound of Formula I. In yet another embodiment, the pharmaceutically acceptable salt is a mesylate of the compound of Formula I. In yet another embodiment, the pharmaceutically acceptable salt is an esylate of the compound of Formula I. In yet another embodiment, the pharmaceutically acceptable salt is an edisylate of the compound of Formula I. In yet another embodiment, the pharmaceutically acceptable salt is a besylate of the compound of Formula I. In yet another embodiment, the pharmaceutically acceptable salt is a tosylate of the compound of Formula I. In still another embodiment, the pharmaceutically acceptable salt is a napsylate of the compound of Formula I. The pharmaceutically acceptable salt of the compound of Formula I can be prepared according to the method described in U.S. patent application Ser. No. 12/233,906, filed Sep. 19, 2008, published as U.S. Pub. No. 2009/0131426 on May 21, 2009; which is incorporated herein by reference in its entirety. The pharmaceutically acceptable salt of the compound of Formula I can also be prepared using other methods known in the art.

As used herein, the compound of Formula I is intended to encompass all possible stereoisomers, unless a particular stereochemistry is specified. Where structural isomers of the compound of Formula I are interconvertible via a low energy barrier, the compound of Formula I may exist as a single tautomer or a mixture of tautomers. This can take the form of proton tautomerism in the compound that contains, e.g., a urea group; or so-called valence tautomerism in the compound that contain an aromatic moiety.

Pharmaceutical Compositions

In certain embodiments, provided herein are pharmaceutical compositions, which comprise the compound of Formula I, or a pharmaceutically acceptable salt or solvate thereof, as an active ingredient, in combination with one or more pharmaceutically acceptable carriers. In certain embodiments, the pharmaceutical composition comprises at least one antigelling agent. In certain embodiments, the pharmaceutical composition comprises at least one nonrelease controlling excipients or carriers. In certain embodiments, the pharmaceutical composition comprises at least one release controlling and at least one nonrelease controlling excipients or carriers. In certain embodiments, the pharmaceutical compositions provided herein are spray-dried compositions. In certain embodiments, the pharmaceutical composition is formulated as a spray-dried composition which comprises at least one antigelling agent.

In certain embodiments, provided herein are pharmaceutical compositions, which comprise the compound of Formula I, or a pharmaceutically acceptable salt or solvate thereof, as an active ingredient, in combination with one or more pharmaceutically acceptable carriers, each of which is selected from the group consisting of hydroxypropyl-β-cyclodextrin, mannitol, sodium starch glycolate (EXPLOTAB®), citric acid, PEG400, PEG6000, polyvinylpyrrolidone (PVP), lauroyl polyoxylglycerides (GELUCIRE® 44/14, Gattefosse Corp., Paramus, N.J.), PLURONIC® F68, silicone dioxide, and water. PLURONIC® F68 (also known as Poloxamer 188) is a block copolymer of ethylene oxide and propylene oxide.

In yet another embodiment, provided herein is a pharmaceutical composition which comprises the compound of Formula I, or a pharmaceutically acceptable salt or solvate thereof, and hydroxypropyl-β-cyclodextrin (HPBCD). In certain embodiments, the HPBCD-containing composition is formulated as an aqueous solution, which is obtained by adding an aqueous HPBCD solution at a desired concentration to the appropriate amount of the compound of Formula I, or a pharmaceutically acceptable salt or solvate thereof, to achieve a desired final concentration of the compound, including, but not limited to, final concentrations of about 1, about 2, about 3, about 5, about 10, about 15, about 50, or about 100 mg/mL. In certain embodiments, the HPBCD composition contains about 5% HPBCD. In certain embodiments, the HPBCD composition contains about 22% HPBCD. In certain embodiments, the pharmaceutical composition contains 2, 3, or 5 mg/mL of a compound of Formula I, or a pharmaceutically acceptable salt or solvate thereof, in 5% HPBCD. In certain embodiments, the pharmaceutical composition contains 1, 3, or 10 mg/mL of a compound of Formula I, or a pharmaceutically acceptable salt or solvate thereof, in 22% HPBCD. Exemplary pharmaceutical compositions are shown in Table 1.

TABLE 1

| Component | Formulation Ia (2 mg/mL Preparation) | Formulation Ib (5 mg/mL Preparation) |
|---|---|---|
| A compound of Formula I or a pharmaceutically acceptable salt or solvate thereof in vial (mg) | 50 mg | 50 mg |
| HPBCD (5% stock, freshly prepared) | 25 mL | 10 mL |

In yet another embodiment, provided herein is a pharmaceutical composition for reconstitution with an aqueous solution that comprises one or more pharmaceutically acceptable carriers, prior to administration. In certain embodiments, the pharmaceutical composition comprises the compound of Formula I, or a pharmaceutically acceptable salt or solvate thereof. In certain embodiments, the pharmaceutical composition comprises the compound of Formula I or a pharmaceutically acceptable salt or solvate thereof in a vial. In yet another embodiment, the pharmaceutical composition comprises from about 1 to about 200 mg, from about 10 to about 100 mg, or from about 10 to 60 mg, or 10 mg, 12 mg, 14 mg, 16 mg, 18 mg, 20 mg, 25 mg, 27 mg, 30 mg, 35 mg, 40 mg, 45 mg, 50 mg, 55 mg, or 60 mg of the compound, or a pharmaceutically acceptable salt or solvate thereof. In certain embodiments, the aqueous solution used for reconstitution comprises HPBCD. In certain embodiments, the aqueous solution comprises 5% by weight of HPBCD. In certain embodiments, the aqueous solution comprises 22% by weight of HPBCD.

In yet another embodiment, provided herein is a pharmaceutical composition, which comprises the compound of Formula I, or a pharmaceutically acceptable salt or solvate thereof, in combination with PEG 400 and water. In certain embodiments, the ratio between PEG400 and water is 3 to 1.

In yet another embodiment, provided herein is a pharmaceutical composition, which comprises the compound of Formula I, or a pharmaceutically acceptable salt or solvate thereof, in combination with mannitol and EXPLOTAB®. In certain embodiments, the pharmaceutical composition is formulated as capsules. Exemplary pharmaceutical compositions are shown in Table 2.

TABLE 2

| Component | Formulation IIa | Formulation IIb |
|---|---|---|
| A compound of Formula I or a pharmaceutically acceptable salt or solvate thereof | 75 mg | 25 mg |
| Mannitol | 282 mg | 332 mg |
| EXPLOTAB ® | 22.8 mg | 22.8 mg |

In yet another embodiment, provided herein is a pharmaceutical composition, which comprises the compound of Formula I, or a pharmaceutically acceptable salt or solvate thereof, in combination with mannitol, EXPLOTAB®, and citric acid. In certain embodiments, the pharmaceutical composition is formulated as capsules. In certain embodiments, the compound of Formula I, or a pharmaceutically acceptable salt or solvate thereof, is micronized, e.g., using jet-mill. Exemplary pharmaceutical compositions are shown in Table 3.

TABLE 3

| Component | Formulation IIIa | Formulation IIIb |
|---|---|---|
| A compound of Formula I or a pharmaceutically acceptable salt or solvate thereof | 75 mg | 25 mg |
| Mannitol | 206 mg | 309 mg |
| EXPLOTAB ® | 22.8 mg | 22.8 mg |
| Citric acid | 76 mg | 25 mg |

In yet another embodiment, provided herein is a pharmaceutical composition, which comprises the compound of Formula I, or a pharmaceutically acceptable salt or solvate thereof, in combination with PEG6000, mannitol, and EXPLOTAB®. In certain embodiments, the pharmaceutical composition is formulated as capsules. Exemplary pharmaceutical compositions are shown in Table 4.

TABLE 4

| Component | Formulation IVa | Formulation IVb |
| --- | --- | --- |
| A compound of Formula I or a pharmaceutically acceptable salt or solvate thereof | 50 mg | 30 mg |
| PEG6000 | 113 mg (31%) | 70.5 mg (18.8%) |
| Mannitol | 158 mg (43.3%) | 229.5 mg (61.2%) |
| EXPLOTAB® | 44 (12%) | 45 mg (12%) |

In yet another embodiment, provided herein is a pharmaceutical composition, which comprises the compound of Formula I, or a pharmaceutically acceptable salt or solvate thereof, in combination with polyvinylpyrrolidone (PVP), mannitol, and EXPLOTAB®. In certain embodiments, the pharmaceutical composition is formulated as capsules. Exemplary pharmaceutical compositions are shown in Table 5.

TABLE 5

| Component | Formulation Va | Formulation Vb |
| --- | --- | --- |
| A compound of Formula I or a pharmaceutically acceptable salt or solvate thereof | 75 mg | 25 mg |
| Mannitol | 226 mg | 276 mg |
| PVP | 14 mg | 14 mg |
| EXPLOTAB® | 35 mg | 35 mg |

In yet another embodiment, provided herein is a pharmaceutical composition, which comprises the compound of Formula I, or a pharmaceutically acceptable salt or solvate thereof, in combination with GELUCIRE®. In certain embodiments, the pharmaceutical composition is formulated as capsules. In certain embodiment, the pharmaceutical composition comprises a dihydrochloride of N-(5-tert-butyl-isoxazol-3-yl)-N'-{4-[7-(2-morpholin-4-yl-ethoxy)imidazo[2,1-b][1,3]benzothiazol-2-yl]phenyl}urea and GELUCIRE® 44/14. An exemplary pharmaceutical composition is shown in Table 6.

TABLE 6

| Component | Formulation VI |
| --- | --- |
| A compound of Formula I or a pharmaceutically acceptable salt or solvate thereof | 50 mg |
| GELUCIRE® | 470 mg |

In yet another embodiment, provided herein is a pharmaceutical composition, which comprises the compound of Formula I, or a pharmaceutically acceptable salt or solvate thereof, in combination with GELUCIRE® and PEG6000. In certain embodiments, the pharmaceutical composition is formulated as capsules. In certain embodiments, the pharmaceutical composition comprises three parts by weight of GELUCIRE® and one parts by weight of PEG6000.

In yet another embodiment, provided herein is a pharmaceutical composition, which comprises the compound of Formula I, or a pharmaceutically acceptable salt or solvate thereof, in combination with mannitol, EXPLOTAB®, and PLURONIC® F68. In certain embodiments, the pharmaceutical composition is formulated as capsules. An exemplary pharmaceutical composition is shown in Table 7.

TABLE 7

| Component | Formulation VII |
| --- | --- |
| A compound of Formula I or a pharmaceutically acceptable salt or solvate thereof | 75 mg |
| Mannitol | 275.5 mg |
| EXPLOTAB® | 22.8 mg |
| PLURONIC® F68 | 11.4 mg |

In yet another embodiment, provided herein is a pharmaceutical composition, which comprises the compound of Formula I, or a pharmaceutically acceptable salt or solvate thereof, in combination with GELUCIRE®, PEG6000, silicone dioxide, mannitol, and EXPLOTAB®. In certain embodiments, the pharmaceutical composition is formulated as capsules. An exemplary pharmaceutical composition is shown in Table 8.

TABLE 8

| Component | Formulation VIII |
| --- | --- |
| A compound of Formula I or a pharmaceutically acceptable salt or solvate thereof | 60 mg |
| GELUCIRE® | 37.5 mg |
| PEG 6000 | 112.5 mg |
| Silicone dioxide | 10 mg |
| Mannitol | 117.5 |
| EXPLOTAB® | 37.5 mg |

In yet another embodiment, provided herein is a pharmaceutical composition, which comprises the compound of Formula I, or a pharmaceutically acceptable salt or solvate thereof, in combination with HPBCD, mannitol, and EXPLOTAB®. In certain embodiments, the pharmaceutical composition is formulated as capsules. An exemplary pharmaceutical composition is shown in Table 9.

TABLE 9

| Component | Formulation IX |
| --- | --- |
| Compound of Formula I or a pharmaceutically acceptable salt or solvate thereof | 70 mg |
| HPBCD | 140 mg |
| Mannitol | 119 mg |
| EXPLOTAB® | 21 mg |

In still another embodiment, provided herein is a pharmaceutical composition, which comprises the compound of Formula I, or a pharmaceutically acceptable salt or solvate thereof, in combination with HPBCD. In certain embodiments, the pharmaceutical composition is formulated as lyophilized powder. In certain embodiments, the compound of Formula I or a pharmaceutically acceptable salt or solvate thereof used in the pharmaceutical composition is a cocrystal of the compound of Formula I, or a pharmaceutically acceptable salt or solvate thereof, and HPBCD. As used here, the term "cocrystal" refers to a crystal containing two or more distinct molecular components within the crystal lattice (unit cell). An exemplary pharmaceutical composition is shown in Table 10.

TABLE 10

| Component | Formulation Xa | Formulation Xb | Formulation Xc |
|---|---|---|---|
| Compound of Formula I or a pharmaceutically acceptable salt or solvate thereof | 10 mg | 10 mg | 75 mg |
| HPBCD | 110 mg | 50 mg | 75 mg |

In certain embodiments, provided herein is a spray-dried pharmaceutical composition which comprises the compound of Formula I, or a pharmaceutically acceptable salt or solvate thereof, and HPBCD. In certain embodiments, the spray-dried composition is obtained by spray drying an aqueous solution of the compound of Formula I, or a pharmaceutically acceptable salt or solvate thereof, and at least one antigelling agent. In certain embodiments, the aqueous solution is obtained by adding an aqueous HPBCD solution at a desired concentration to the appropriate amount of the compound of Formula I, or a pharmaceutically acceptable salt or solvate thereof, to achieve a desired final concentration of the compound, including, but not limited to, final concentrations of about 1, about 2, about 3, about 5, about 10, about 15, about 30, about 40, about 50, about 75, or about 100 mg/mL. In certain embodiments, the compositions provided herein comprise about 5% HPBCD. In certain embodiments, the compositions provided herein comprise about 22% HPBCD. In certain embodiments, the compositions provided herein comprise about 20% HPBCD. In certain embodiments, the compositions provided herein comprise about 40% HPBCD. In certain embodiments, the compositions provided herein comprise about 50% HPBCD. In certain embodiments, the compositions provided herein comprise 20, 30, 40, 45, or 50 mg of a compound of Formula I, or a pharmaceutically acceptable salt or solvate thereof, in each mL of 30, 40 or 50% HPBCD. In certain embodiments, the compositions provided herein comprise 30, 40, or 50 mg of a compound of Formula I, or a pharmaceutically acceptable salt or solvate thereof, in each mL of 40% HPBCD. In certain embodiments, the compositions provided herein comprise about 40 mg of a compound of Formula I, or a pharmaceutically acceptable salt or solvate thereof, in each mL of about 40% HPBCD.

In certain embodiments, the compositions provided herein comprise the compound of Formula I or a pharmaceutically acceptable salt or solvate thereof and HPBCD in a ratio of about 1:5, 1:7, 1:10, 1:13, 1:15, or 1:20 by weight. In certain embodiments, the compositions provided herein comprise the compound of Formula I or a pharmaceutically acceptable salt or solvate thereof and HPBCD in a ratio of about 1:10 by weight. In an exemplary embodiment, about 1.1 g spray-dried composition provided herein comprises about 100 mg of the compound of Formula I or a pharmaceutically acceptable salt or solvate thereof and about 1000 mg of HPBCD. In another exemplary embodiment, about 2.2 g spray-dried composition provided herein comprises about 200 mg of the compound of Formula I or a pharmaceutically acceptable salt or solvate thereof and about 2000 mg of HPBCD.

In certain embodiments, provided herein is a spray-dried pharmaceutical composition for reconstitution with an aqueous solution, prior to administration. In certain embodiments, the spray-dried pharmaceutical composition in a vial. In certain embodiments, the spray-dried compositions provided herein are reconstituted with water to provide an aqueous solution comprising about 1-10, 2-10, 3-10, 2-8, or 3-7 mg of the spray-dried composition per mL of water. In certain embodiments, the spray-dried compositions provided herein are reconstituted with water to provide an aqueous solution comprising about 1, 2, 3, 4, 5, 6, 7, 8, 9 or 10 mg of the spray-dried composition per mL of water.

In certain embodiments, the pharmaceutical compositions provided herein are formulated in a dosage from about 1 to about 100 mg, or from about 1 to about 60 mg, or from about 10 to about 60 mg, from about 10 to about 40 mg, from about 10 to about 27 mg, or from about 10 to about 25 mg of the compound of Formula I, or a pharmaceutically acceptable salt or solvate thereof.

In certain embodiments, the compound of Formula I or a pharmaceutically acceptable salt or solvate thereof used in the pharmaceutical compositions provided herein is in a solid form. Suitable solid forms include, but are not limited to, solid forms comprising the free base of the compound of Formula I, and solid forms comprising salts of the compound of Formula I, including, but not limited to, HCl salts, HBr salts, sulfate salts, mesylate salts, esylate salts, edisylate salts, besylate salts, tosylate salts, and napsylate salts. In certain embodiments, the HCl salts of the compound of Formula I include mono-HCl salts and bis-HCl salts. In certain embodiments, solid forms provided herein include polymorphs, solvates (including hydrates), and cocrystals comprising the compound of Formula I and/or salts thereof. In certain embodiments, the solid form is a cocrystal of the compound of Formula I, or a pharmaceutically acceptable salt or solvate thereof, and HPBCD. In certain embodiments, the compound of Formula I used in the pharmaceutical compositions provided herein is a dihydrochloride salt of N-(5-tert-butyl-isoxazol-3-yl)-N'-{4-[7-(2-morpholin-4-yl-ethoxy)imidazo[2,1-b][1,3]benzothiazol-2-yl]phenyl}urea. Some of these solid forms are described in U.S. Provisional App. Ser. No. 60/994,635, filed Sep. 19, 2007; patent application Ser. No. 12/233,906, filed Sep. 19, 2008, published as U.S. Pub. No. 2009/0131426 on May 21, 2009,; each of which is incorporated herein by reference in its entirety.

The pharmaceutical compositions provided herein may be formulated in various dosage forms for al, parenteral, and topical administration. The pharmaceutical compositions may also be formulated as modified release dosage forms, including delayed-, extended-, prolonged-, sustained-, pulsed-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Deliver Technology*, Rathbone et al., Eds., Drugs and the Pharmaceutical Science, Marcel Dekker, Inc.: New York, N.Y., 2003; Vol. 126).

In certain embodiments, the pharmaceutical compositions are provided in a dosage form for al administration. In certain embodiments, the pharmaceutical compositions are provided in a dosage form for parenteral administration. In yet another embodiment, the pharmaceutical compositions are provided in a dosage form for topical administration.

The pharmaceutical compositions provided herein may be provided in a unit-dosage form or multiple-dosage form. A unit-dosage form, as used herein, refers to a physically discrete unit suitable for administration to human and animal subjects, and packaged individually as is known in the art. Each unit-dose contains a predetermined quantity of the active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein may be administered at once or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

Further to these discussed above, the pharmaceutical compositions provided herein may be provided in solid, semi-solid, or liquid dosage forms for al administration. As used herein, oral administration also includes buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG) (e.g., PEG400 and PEG6000); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica (silicone dioxide) or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (e.g., TWEEN® 20), poloxamers (e.g., PLURONIC® F68), polyoxyethylene sorbitan monooleate 80 (e.g., TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, polyvinylpyrrolidone, and lauroyl polyoxylglycerides (e.g., GELUCIRE® 44/14). Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

Suitable antigelling agents include, but are not limited to, cyclodextrins, including α-cyclodextrin, β-cyclodextrin, hydroxypropyl-β-cyclodextrin, sulfobutylether-β-cyclodextrin, sulfobutylether 7-β-cyclodextrin (CAPTISOL®, CyDex, Lenexa, Kans.), propane-1,2-diol, trisodium sulfosuccinate, citric acid and water soluble citrate.

It should be understood that many carriers and excipients may serve several functions, even within the same formulation.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action.

B. Parenteral Administration

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable antigelling agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.), propane-1,2-diol, trisodium sulfosuccinate, citric acid and water soluble citrate.

The pharmaceutical compositions provided herein may be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In certain embodiments, the pharmaceutical compositions are provided as ready-to-use sterile solutions. In certain embodiments, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein may be formulated as immediate or modified release dosage forms, including delayed-, sustained, pulsed-, controlled, targeted-, and programmed-release forms.

The pharmaceutical compositions may be formulated as a suspension, solid, semi-solid, or thixotropic liquid, for administration as an implanted depot. In certain embodiments, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

The pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; and nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

The pharmaceutical compositions provided herein may be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

The pharmaceutical compositions provided herein for topical administration may be formulated to be immediate release or modified release, including delayed-, sustained-, pulsed-, controlled-, targeted, and programmed release.

Methods of Use

In certain embodiments, provided herein is a method of treating acute myeloid leukemia in a patient, which comprises administering to the patient having acute myeloid leukemia a therapeutically effective amount of the compound of Formula I or a pharmaceutically acceptable salt or solvate thereof, wherein the patient is relapsed or refractory to a prior cancer therapy. In certain embodiments, the patient is relapsed after a first, second, third or subsequent cancer therapy.

In certain embodiments, the patient is 60 years or older and relapsed after a first line cancer therapy. In certain embodiments, the patient is 18 years or older and is relapsed or refractory after a second line cancer therapy. In certain embodiments, the patient is 18 years or older and is relapsed or refractory after a third or subsequent line cancer therapy. In certain embodiments, the patient is 60 years or older and is refractory to a first line cancer therapy. In certain embodiments, the patient is 70 years or older and is previously untreated. In certain embodiments, the patient is 70 years or older and is ineligible and/or unlikely to benefit from cancer therapy.

In certain embodiments, the patients previously untreated who are ineligible and/or unlikely to benefit from cancer therapy include patients having at least one of the following adverse factors: prior MDS (myelodysplastic syndrome), unfavorable cytogenetics at diagnosis, ECOG (Eastern Cooperative Oncology Group) performance status 1, 2 or 3, or ≥75 years of age.

In certain embodiments, the patient is
a) 60 years or older and relapsed after a first line cancer therapy,
b) 60 years or older and is refractory to a first line cancer therapy,
c) 18 years or older and is relapsed or refractory after a second line cancer therapy, or
d) 70 years or older and is previously untreated who is ineligible and/or unlikely to benefit from cancer therapy.

In certain embodiments, the patient is relapsed after a third-line cancer therapy or a salvage therapy.

In certain embodiments, acute myeloid leukemia is resistant or refractory to cancer therapy drugs currently used to treat AML or are currently in clinical trials for treatment of AML. In certain embodiments, acute myeloid leukemia is resistant or refractory to PKC-412, MLN-518, CEP-701, CT 53518, CT-53608, CT-52923, D-64406, D-65476, AGL-2033, AG1295, AG1296, KN-1022, KW-2449, SU5416, SU5614, SU11248 (sunitinib), L-00021649, BAY-43-9006 (sorafenib), imatinib, CHIR-258, cytarabine, clofarabine, azacytidine, daunorubicin, idarubicin, thioguanine, etoposide, decitabine, fludarabine, mitoxantrone, pixantrone, doxorubicin, etoposide, vorinostat, sapacitabine, gemtuzumab ozogamicin, melphalan, oxaliplatin, cisplatin, carboplatin, satraplatin or busulfan.

In certain embodiments, acute myeloid leukemia is resistant or refractory to cytarabine, daunorubicin, idarubicin, mitoxantrone, 6-thioguanine, 6-mercaptopurine, fludarabine, vincristine, etoposide, prednisone or a combination thereof.

In certain embodiments, the patient is 60, 65, 70, 75, 80, 85 or older and relapsed after a first line cancer therapy. In certain embodiments, the patient is 60, 65, 70, 75, 80, 85 or older and is refractory to a first line cancer therapy. In certain embodiments, the patient is 18, 20, 25, 30, 35, 40, 45, 50, 55, 60, 65, 70, 75, 80, 85 or older and relapsed after a second line cancer therapy. In certain embodiments, the patient is 70, 75, 80, 85 or older and is previously untreated who is ineligible and/or unlikely to benefit from cancer therapy.

In certain embodiments, the patients previously untreated who are ineligible and/or unlikely to benefit from chemotherapy include patients having at least one of the following adverse factors: prior MDS (myelodysplastic syndrome), unfavorable cytogenetics at diagnosis, ECOG (Eastern Cooperative Oncology Group) performance status 2, or ≥75 years of age.

In some embodiments, the patient is treated based on the Eastern Cooperative Oncology Group (ECOG) performance status score of the patient for leukemia. ECOG performance status can be scored on a scale of 0 to 5, with 0 denoting asymptomatic; 1 denoting symptomatic but completely ambulant; 2 denoting symptomatic and <50% in bed during the day; 3 denoting symptomatic and >50% in bed, but not bed bound; 4 denoting bed bound; and 5 denoting death. In some embodiments, the patient has an ECOG performance status score of 0, 1, 2 or 3. In other embodiments, the patient has an ECOG performance status score of 0, 1 or 2. In other embodiments, the patient has an ECOG performance status score of 1 or 2. In some embodiments, the patient has an ECOG performance status score of 2 or 3. In other embodiments, the patient has an ECOG performance status score of 2.

In certain embodiments, provided herein is a method of treating a proliferative disease in a mammal, which comprises administering to the mammal having or suspected to have the proliferative disease, a therapeutically effective amount of the compound of Formula I or a pharmaceutically acceptable salt or solvate thereof, wherein the therapeutically effective amount is at least about 12 mg per day, and wherein the compound is administered on an empty stomach.

In certain embodiments, the methods provided herein comprise administering the compound at least about 2, 3, 4, 5, 6, 7, 8, 9, 10, 11 or 12 hours after meal. In certain embodiments, the compound is administered about 1, 2, 3, 4, 5 or 6 hours before meal. In certain embodiments, the compound is administered at least about 2 hours after meal and about 1 hour or more before meal.

In certain embodiments, the methods provided herein encompass treating a subject regardless of patient's age, although some diseases or disorders are more common in certain age groups. Further provided herein is a method for treating a subject who has undergone surgery in an attempt to treat the disease or condition at issue, as well as the one who have not. Because the subjects with cancer have heterogeneous clinical manifestations and varying clinical outcomes, the treatment given to a particular subject may vary, depending on his/her prognosis. The skilled clinician will be able to readily determine without undue experimentation, specific secondary agents, types of surgery, and types of non-drug based standard therapy that can be effectively used to treat an individual subject with cancer.

In certain embodiments, the methods provided herein are used to treat heavily pretreated patients. A heavily pretreated patient is defined as a patient who has been treated previously with, for example, three or more than three courses of a cancer therapy. In certain embodiments, heavily pretreated patient has been treated with 3, 4, 5, 6, 7, 8, 9 or 10 cancer therapy treatment regimens. The heavily pretreated patient could be pretreated by any cancer therapy regime deemed suitable by one of skill in the art. In certain embodiments, the heavily pretreated patients had been previously treated with one or more FLT3 inhibitors, for example, CEP701, PKC412, MLN-518, sunitinib and sorafenib.

In certain embodiments, the methods provided herein are used to treat minimally pretreated patients. Patients, who have not been treated previously or have been treated but are not considered heavily pretreated, are minimally pretreated patients.

In certain embodiments, the therapeutically effective amount is a range from about 12 to about 1,000 mg per day, from about 12 to about 500 mg per day, from about 12 to about 450 mg per day, from about 12 to about 300 mg per day, from about 12 to about 200 mg per day, from about 12 to about 100 mg per day, from about 12 to about 90 mg per day, from about 12 to about 80 mg per day, from about 12 to about 70 mg per day, from about 15 to about 65 mg per day, or from about 20 to about 60 mg per day. In certain embodiments, the therapeutically effective amount is from about 12 to about 1,000 mg per day. In certain embodiments, the therapeutically effective amount is from about 12 to about 500 mg per day. In yet another embodiment, the therapeutically effective amount is from about 12 to about 450 mg per day. In yet another embodiment, the therapeutically effective amount is from about 12 to about 400 mg per day. In yet another embodiment, the therapeutically effective amount is from about 12 to about 300 mg per day. In yet another embodiment, the therapeutically effective amount is from about 12 to about 200 mg per day. In yet another embodiment, the therapeutically effective amount is from about 12 to about 150 mg per day. In yet another embodiment, the therapeutically effective amount is from about 12 to about 100 mg per day. In yet another embodiment, the therapeutically effective amount is from about 12 to about 90 mg per day. In yet another embodiment, the therapeutically effective amount is from about 12 to about 80 mg per day. In yet another embodiment, the therapeutically effective amount is from about 12 to about 70 mg per day. In yet another embodiment, the therapeutically effective amount is from about 15 to about 65 mg per day. In still another embodiment, the therapeutically effective amount is from about 20 to about 60 mg per day.

In certain embodiments, the therapeutically effective amount is about 12, about 18, about 20, about 25, about 27, about 30, about 35, about 40, about 45, about 50, about 55, about 60, about 90, about 100, about 135, about 150, about 200, about 300, or about 450 mg per day. In certain embodiments, the therapeutically effective amount is about 12 mg per day. In certain embodiments, the therapeutically effective amount is about 18 mg per day. In yet another embodiment, the therapeutically effective amount is about 20 mg per day. In yet another embodiment, the therapeutically effective amount is about 25 mg per day. In yet another embodiment, the therapeutically effective amount is about 27 mg per day. In yet another embodiment, the therapeutically effective amount is about 30 mg per day. In yet another embodiment, the therapeutically effective amount is about 35 mg per day. In yet another embodiment, the therapeutically effective amount is about 40 mg per day. In yet another embodiment, the therapeutically effective amount is about 45 mg per day. In yet another embodiment, the therapeutically effective amount is about 50 mg per day. In yet another embodiment, the therapeutically effective amount is about 55 mg per day. In yet another embodiment, the therapeutically effective amount is about 60 mg per day. In yet another embodiment, the therapeutically effective amount is about 90 mg per day. In yet another embodiment, the therapeutically effective amount is about 100 mg per day. In yet another embodiment, the therapeutically effective amount is about 135 mg per day. In yet another embodiment, the therapeutically effective amount is about 150 mg per day. In yet another embodiment, the therapeutically effective amount is about 200 mg per day. In yet another embodiment, the therapeutically effective amount is about 300 mg per day. In still another embodiment, the therapeutically effective amount is about 450 mg per day.

In certain embodiments, the therapeutically effective amount is 90 mg per day for a female patient and 135 mg per day for a male patient. In certain embodiments, the therapeutically effective amount is 135 mg per day for a female patient and 200 mg per day for a male patient.

In certain embodiments, the therapeutically effective amount is a range from about 0.2 to about 20 mg/kg/day, from about 0.2 to about 15 mg/kg/day, from about 0.2 to about 10 mg/kg/day, from about 0.2 to about 9 mg/kg/day, from about 0.2 to about 8 mg/kg/day, from about 0.2 to about 7 mg/kg/day, from about 0.2 to about 6 mg/kg/day, from about 0.2 to about 5 mg/kg/day, from about 0.2 to about 5 mg/kg/day, from about 0.2 to about 5 mg/kg/day, from about 0.2 to about 4 mg/kg/day, from about 0.2 to about 3 mg/kg/day, from about 0.2 to about 2 mg/kg/day, from about 0.2 to about 1 mg/kg/day, or from about 0.24 mg/kg/day to about 9 mg/kg/day.

In certain embodiments, the therapeutically effective amount is from about 0.2 to about 20 mg/kg/day. In certain embodiments, the therapeutically effective amount is from about 0.2 to about 15 mg/kg/day. In yet another embodiment, the therapeutically effective amount is from about 0.2 to about 10 mg/kg/day. In yet another embodiment, the therapeutically effective amount is from about 0.2 to about 9 mg/kg/day. In yet another embodiment, the therapeutically effective amount is from about 0.2 to about 8 mg/kg/day. In yet another embodiment, the therapeutically effective amount is from about 0.2 to about 7 mg/kg/day. In yet another embodiment, the therapeutically effective amount is from about 0.2 to about 6 mg/kg/day. In yet another embodiment, the therapeutically effective amount is from about 0.2 to about 5 mg/kg/day. In yet another embodiment, the therapeutically effective amount is from about 0.2 to about 5 mg/kg/day. In yet another embodiment, the therapeutically effective amount is from about 0.2 to about 4 mg/kg/day. In yet another embodiment, the therapeutically effective amount is from about 0.2 to about 3 mg/kg/day. In yet another embodiment, the therapeutically effective amount is from about 0.2 to about 2 mg/kg/day. In yet another embodiment, the therapeutically effective amount is from about 0.2 to about 1 mg/kg/day. In still another embodiment, the therapeutically effective amount is from about 0.24 to about 9 mg/kg/day.

The administered dose can also be expressed in units other than as mg/kg/day. For example, doses for parenteral administration can be expressed as mg/m$^2$/day. One of ordinary skill in the art would readily know how to convert doses from mg/kg/day to mg/m$^2$/day to given either the height or weight of a subject or both (see, www.fda.gov/cder/cancer/animalframe.htm). For example, a dose of 1 mg/kg/day for a 65 kg human is approximately equal to 38 mg/m$^2$/day.

In certain embodiments, compound I is administered in an amount sufficient to provide a plasma concentration of the compound at steady state, ranging from about 0.0.02 to about 100 µM, from about 0.1 to about 10 µM, from about 0.3 to about 10 µM, from about 0.9 to about 5 µM, from about 1 to about 4 µM, from about 1 to about 3 µM or from about 1.5 to about 3 µM. In certain embodiments, the amount of the compound administered is sufficient to provide a maximum plasma concentration of the compound of about 0.02 to about 100 µM. In certain embodiments, the amount of the compound administered is sufficient to provide a maximum plasma concentration of the compound of about 0.1 to about 10 µM. In yet another embodiment, the amount of the compound administered is sufficient to provide a maximum plasma concentration of the compound of about 0.3 to about 10 µM. In yet another embodiment, the amount of the compound administered is sufficient to provide a maximum plasma concentration of the compound of about 0.9 to about 5 µM. In yet another embodiment, the amount of the compound administered is sufficient to provide a maximum plasma concentration of the compound of about 1 to about 4 µM. In yet another embodiment, the amount of the compound administered is sufficient to provide a maximum plasma concentration of the compound of about 1 to about 3 µM. In yet another embodiment, the amount of the compound administered is sufficient to provide a maximum plasma concentration of the compound of about 1.5 to about 3 µM. As used herein, the term "plasma concentration at steady state" is the concentration reached after a period of administration of a compound. Once steady state is reached, there are minor peaks and troughs on the time dependent curve of the plasma concentration of the compound.

In yet another embodiment, compound I is administered in an amount sufficient to provide a maximum plasma concentration (peak concentration) of the compound, ranging from about 0.0.02 to about 100 µM, from about 0.1 to about 10 µM, from about 0.3 to about 10 µM, from about 0.9 to about 5 µM, from about 1 to about 4 µM, from about 1 to about 3 µM or from about 1.5 to about 3 µM. In certain embodiments, the amount of the compound administered is sufficient to provide a maximum plasma concentration of the compound of about 0.02 to about 100 µM. In certain embodiments, the amount of the compound administered is sufficient to provide a maximum plasma concentration of the compound of about 0.1 to about 10 µM. In yet another embodiment, the amount of the compound administered is sufficient to provide a maximum plasma concentration of the compound of about 0.3 to about 10 µM. In yet another embodiment, the amount of the compound administered is sufficient to provide a maximum plasma concentration of the compound of about 0.9 to about 5 µM. In yet another embodiment, the amount of the compound administered is sufficient to provide a maximum plasma concentration of the compound of about 1 to about 4 µM. In yet another embodiment, the amount of the compound administered is sufficient to provide a maximum plasma concentration of the compound of about 1 to about 3 µM. In yet another embodiment, the amount of the compound administered is sufficient to provide a maximum plasma concentration of the compound of about 1.5 to about 3 µM.

In yet another embodiment, compound I is administered in an amount sufficient to provide a minimum plasma concentration (trough concentration) of the compound, ranging from about 0.02 to about 10 µM, from about 0.1 to about 10 µM, from about 0.3 to about 10 µM, from about 0.6 to about 5 µM, about 0.6 to about 3 µM, from about 0.9 to about 3 µM, or from about 1.5 to about 3 µM, when more than one doses are administered. In certain embodiments, the amount of the compound administered is sufficient to provide a minimum plasma concentration of the compound of about 0.02 to about 10 µM. In certain embodiments, the amount of the compound administered is sufficient to provide a minimum plasma concentration of the compound of about 0.1 to about 10 µM. In yet another embodiment, the amount of the compound administered is sufficient to provide a minimum plasma concentration of the compound of about 0.3 to about 10 µM. In yet another embodiment, the amount of the compound administered is sufficient to provide a minimum plasma concentration of the compound of about 0.6 to about 5 µM. In yet another embodiment, the amount of the compound administered is sufficient to provide a minimum plasma concentration of the compound of about 0.6 to about 3 µM. In yet another embodiment, the amount of the compound administered is sufficient to provide a minimum plasma concentration of the compound of about 0.9 to about 3 µM. In yet another embodiment, the amount of the compound administered is sufficient to provide a minimum plasma concentration of the compound of about 1.5 to about 3 µM.

In still another embodiment, compound I is administered in an amount sufficient to provide an area under the curve (AUC) of the compound, ranging from about 100 to about 50,000 ng*hr/mL, from about 1000 to about 50,000 ng*hr/mL, from about 1500 to about 40,000 ng*hr/mL from about 2,000 to about 35,000 ng*hr/mL, from about 2000 to about 35,000 ng*hr/mL, from about 9,000 to about 35,000 ng*hr/mL, or from about 10,000 to about 25,000 ng*hr/mL.

In certain embodiments, the mammal is a human.

In certain embodiments, the proliferative disease is cancer. In certain embodiments, the cancer is leukemia.

In certain embodiments, the leukemia is chronic lymphocytic leukemia, chronic myelocytic leukemia, acute lymphoblastic leukemia, acute myeloid leukemia, and acute myeloblastic leukemia.

In certain embodiments, the leukemia is acute leukemia. In certain embodiments, the acute leukemia is acute myeloid leukemia (AML). In certain embodiments, acute myeloid leukemia is undifferentiated AML (M0), myeloblastic leukemia (M1), myeloblastic leukemia (M2), promyelocytic leukemia (M3 or M3 variant [M3V]), myelomonocytic leukemia (M4 or M4 variant with eosinophilia [M4E]), monocytic leukemia (M5), erythroleukemia (M6), or megakaryoblastic leukemia (M7). In certain embodiments, the acute myeloid leukemia is undifferentiated AML (M0). In yet another embodiment, the acute myeloid leukemia is myeloblastic leukemia (M1). In yet another embodiment, the acute myeloid leukemia is myeloblastic leukemia (M2). In yet another embodiment, the acute myeloid leukemia is promyelocytic leukemia (M3 or M3 variant [M3V]). In yet another embodiment, the acute myeloid leukemia is myelomonocytic leukemia (M4 or M4 variant with eosinophilia [M4E]). In yet another embodiment, the acute myeloid leukemia is monocytic leukemia (M5). In yet another embodiment, the acute myeloid leukemia is erythroleukemia (M6). In yet another embodiment, the acute myeloid leukemia is megakaryoblastic leukemia (M7). In yet another embodiment, the acute myeloid leukemia is promyelocytic leukemia.

In certain embodiments, the subject has a constitutively activating FLT3 mutatation. In still another embodiment, the constitutively activating FLT3 mutant is a FLT3 ITD mutatation. In yet another embodiment, the leukemia is attributable to a FLT3 internal tandem duplication (ITD) mutation. In certain embodiments, the patient has a high FLT3-ITD allelic ratio. In certain embodiments, the patient has an intermediate FLT3-ITD allelic ratio. In certain embodiments, the patient has a low FLT3-ITD allelic ratio.

In yet another embodiment, the leukemia is attributable to a FLT3 point mutation. In yet another embodiment, the FLT3 point mutation is a missense point mutation. In still another embodiment, the FLT3 point mutation is a point mutation at amino acid D835. In certain embodiments, the methods provided herein are useful in treating subjects with constitutively activating FLT3 mutation.

In certain embodiments, the acute leukemia is acute lymphocytic leukemia (ALL). In certain embodiments, the acute lymphocytic leukemia is leukemia that originates in the blast cells of the bone marrow (B-cells), thymus (T-cells), or lymph nodes. The acute lymphocytic leukemia is categorized according to the French-American-British (FAB) Morphological Classification Scheme as L1—Mature-appearing lymphoblasts (T-cells or pre-B-cells), L2—Immature and pleomorphic (variously shaped) lymphoblasts (T-cells or pre-B-cells), and L3—Lymphoblasts (B-cells; Burkitt's cells). In certain embodiments, the acute lymphocytic leukemia originates in the blast cells of the bone marrow (B-cells). In yet another embodiment, the acute lymphocytic leukemia originates in the thymus (T-cells). In yet another embodiment, the acute lymphocytic leukemia originates in the lymph nodes. In yet another embodiment, the acute lymphocytic leukemia is L1 type characterized by mature-appearing lymphoblasts (T-cells or pre-B-cells). In yet another embodiment, the acute lymphocytic leukemia is L2 type characterized by immature and pleomorphic (variously shaped) lymphoblasts (T-cells or pre-B-cells). In yet another embodiment, the acute lymphocytic leukemia is L3 type characterized by lymphoblasts (B-cells; Burkitt's cells).

In yet another embodiment, the leukemia is T-cell leukemia. In certain embodiments, the T-cell leukemia is peripheral T-cell leukemia, T-cell lymphoblastic leukemia, cutaneous T-cell leukemia, and adult T-cell leukemia. In certain embodiments, the T-cell leukemia is peripheral T-cell leukemia. In yet another embodiment, the T-cell leukemia is T-cell lymphoblastic leukemia. In yet another embodiment, the T-cell leukemia is cutaneous T-cell leukemia. In still another embodiment, the T-cell leukemia is adult T-cell leukemia.

In yet another embodiment, the leukemia is Philadelphia positive. In certain embodiments, the Philadelphia positive leukemia is Philadelphia positive AML, including, but not limited to, undifferentiated AML (M0), myeloblastic leukemia (M1), myeloblastic leukemia (M2), promyelocytic leukemia (M3 or M3 variant [M3V]), myelomonocytic leukemia (M4 or M4 variant with eosinophilia [M4E]), monocytic leukemia (M5), erythroleukemia (M6), or megakaryoblastic leukemia (M7). In certain embodiments, the Philadelphia positive leukemia is Philadelphia positive ALL.

In still another embodiment, the leukemia is refractory or drug resistant. In certain embodiments, the subject has developed drug resistance to the anticancer therapy. In certain embodiments, the subject has developed drug resistance to a FLT3 kinase inhibitor.

In another embodiment, the proliferative disease is MDS. In certain embodiments, the subject is an AML patient who did not have prior MDS. In certain embodiments, the subject is an AML patient who had prior MDS.

In certain embodiments, the subject to be treated with one of the methods provided herein has not been treated with anticancer therapy prior to the administration of the compound of Formula I, or a pharmaceutically acceptable salt or solvate thereof. In certain embodiments, the subject 1 to be treated with one of the methods provided herein has been treated with anticancer therapy prior to the administration of the compound of Formula I, or a pharmaceutically acceptable salt or solvate thereof. In certain embodiments, the subject to be treated with one of the methods provided herein has been treated with a FLT3 kinase inhibitor. In yet another embodiment, the subject has been treated with one or more cancer therapy drugs currently used to treat AML or are currently in clinical trials for treatment of AML. In another embodiment, the subject received a HSCT prior to the administration of the compound of Formula I. In yet another embodiment, the subject has not received a HSCT prior to the administration of the compound of Formula I.

In certain embodiments, the subject to be treated with one of the methods provided herein has been treated with PKC 412, MLN 518, CEP-701, CT 53518, CT-53608, CT-52923, D-64406, D-65476, AGL-2033, AG1295, AG1296, KN-1022, KW-2449, SU5416, SU5614, SU11248 (sunitinib), L-00021649, BAY-43-9006 (sorafenib) CHIR-258, cytarabine, clofarabine, azacytidine, daunorubicin, idarubicin, etoposide, decitabine, fludarabine, mitoxantrone, pixantrone, doxorubicin, etoposide, thioguanine, vorinostat, sapacitabine, gemtuzumab ozogamicin, melphalan, oxaliplatin, cisplatin, carboplatin, satraplatin or busulfan or others known or approved therapeutic agents for treating AML or ALL.

In yet another embodiment, provided herein is a method of treating acute myeloid leukemia in a patient, which comprises the steps of (i) determining a patient's peripheral blast cell count, bone marrow blast cell count, phosphorylated STAT5 levels or phosphorylated FLT3 levels, (ii) administering to the patient having acute myeloid leukemia the compound of Formula I or a pharmaceutically acceptable salt or solvate thereof, (iii) determining after the first dose, the patient's peripheral blast cell count, bone marrow blast cell count, phosphorylated STAT5 levels or phosphorylated FLT3 levels, and (iv) resuming administration of AC220 if the patient is found to have a decreased blast count or decreased levels of phosphorylated STAT5 or FLT3. In certain embodiments, the assessment of the patient's response to AC220 is made 30 minutes, 1 hour, 2 hours, 4 hours, 6 hours or 24 hours after the first dose. In certain embodiments, the assessment of the patient's response to AC220 is made 24 hours after the first dose. In certain embodiments, the assessment of the patient's response to AC220 is made 48 hours after the first dose. In certain embodiments, the assessment of the patient's response to AC220 is made 8 days after the first dose. In certain embodiments, phosphorylated FLT3 may be measured using the methods described in PCT/US2009/063534.

In certain embodiments, the cancer that can be treated with the methods provided herein includes, but is not limited to, bladder cancer, breast cancer, cervical cancer, colon cancer (e.g., colorectal cancer), esophageal cancer, head and neck cancer, liver cancer, lung cancer (e.g., small cell and non-small cell lung cancers), melanoma, myeloma, neuroblastoma, ovarian cancer, pancreatic cancer, prostate cancer, renal cancer, sarcoma (e.g., osteosarcoma), skin cancer (e.g., squamous cell carcinoma), stomach cancer, testicular cancer, thyroid cancer, uterine cancer, gastrointestinal stromal tumor (GIST), melanoma, mast cell tumor, neuroblastoma and germ cell tumor.

In certain embodiments, the cancer is a metastatic cancer, including, but not limited to, bladder cancer, breast cancer, cervical cancer, colon cancer (e.g., colorectal cancer), esophageal cancer, head and neck cancer, liver cancer, lung cancer (e.g., small cell and non-small cell lung cancers), melanoma, myeloma, neuroblastoma, ovarian cancer, pancreatic cancer, prostate cancer, renal cancer, sarcoma (e.g., osteosarcoma), skin cancer (e.g., squamous cell carcinoma), stomach cancer, testicular cancer, thyroid cancer, and uterine cancer. In certain embodiments, the metastatic cancer is breast or prostate cancer. In certain embodiments, the metastatic cancer is breast cancer. In yet another embodiment, the metastatic cancer is prostate cancer. In certain embodiments, the cancer is a metastatic cancer, where the primary cancer is blood borne.

In certain embodiments, the cancer treatable by the methods provided herein is a KIT kinase mediated cancer.

In certain embodiments, the methods provided herein are useful in treatment of infectious diseases mediated either via viral or bacterial pathogens and sepsis, including KIT-mediated sepsis.

In the methods provided herein, the compound of Formula I, or a pharmaceutically acceptable salt or solvate thereof, may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. The compound of Formula I, or a pharmaceutically acceptable salt or solvate thereof, may be formulated, alone or together, in suitable dosage unit with pharmaceutically acceptable excipients, carriers, adjuvants and vehicles, appropriate for each route of administration. Exemplary formulation are described in U.S. application Ser. No. 12/267,321, which is incorporated by reference in its entirety.

In certain embodiments, the compound of Formula I, or a pharmaceutically acceptable salt or solvate thereof, is administered orally. In certain embodiments, the compound of Formula I, or a pharmaceutically acceptable salt or solvate thereof, is administered parenterally. In yet another embodiment, the compound of Formula I, or a pharmaceutically acceptable salt or solvate thereof, is administered intravenously.

The compound of Formula I, or a pharmaceutically acceptable salt or solvate thereof can be delivered as a single dose such as, e.g., a single bolus injection, or al tablets or pills; or over time such as, e.g., continuous infusion over time or divided bolus doses over time. The compound can be administered repetitively if necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement. Response Evaluation Criteria in Solid Tumors (RECIST) Guidelines, *Journal of the National Cancer Institute* 92(3): 205-216 (2000). Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

The compound of Formula I, or a pharmaceutically acceptable salt or solvate thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest that is no drug). As used herein, the term "daily" is intended to mean that a therapeutic compound, such as the compound of Formula I or a pharmaceutically acceptable salt or solvate thereof, is administered once or more than once each day, for example, for a period of time. The term "continuous" is intended to mean that a therapeutic compound, such as the compound of Formula I or a pharmaceutically acceptable salt or solvate thereof, is administered daily for an uninterrupted period of at least 10 days to 52 weeks. The term "intermittent" or "intermittently" as used herein is intended to mean stopping and starting at either regular or irregular intervals. For example, intermittent administration of the compound of Formula I or a pharmaceutically acceptable salt or solvate thereof is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as the compound of Formula I or a pharmaceutically acceptable salt or solvate thereof, is administered daily or continuously but with a rest period.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In certain embodiments, the compound of Formula I, or a pharmaceutically acceptable salt or solvate thereof, is administered once a day. In certain embodiments, The compound of Formula I, or a pharmaceutically acceptable salt or solvate thereof, is administered twice a day. In yet another embodiment, The compound of Formula I, or a pharmaceutically acceptable salt or solvate thereof, is administered three times a day. In still another embodiment, The compound of Formula I, or a pharmaceutically acceptable salt or solvate thereof, is administered four times a day.

In certain embodiments, the compound of Formula I, or a pharmaceutically acceptable salt or solvate thereof, is administered once per day from one day to six months, from one week to three months, from one week to four weeks, from one week to three weeks, or from one week to two weeks. In certain embodiments, the compound of Formula I, or a pharmaceutically acceptable salt or solvate thereof, is administered once per day for one week, two weeks, three weeks, or four weeks. In certain embodiments, the compound of Formula I, or a pharmaceutically acceptable salt or solvate thereof, is administered once per day for one week. In certain embodiments, the compound of Formula I, or a pharmaceutically acceptable salt or solvate thereof, is administered once per day for two weeks. In yet another embodiment, the compound of Formula I, or a pharmaceutically acceptable salt or solvate thereof, is administered once per day for three weeks. In still another embodiment, the compound of Formula I, or a pharmaceutically acceptable salt or solvate thereof, is administered once per day for four weeks.

In certain embodiments, the compound of Formula I, or a pharmaceutically acceptable salt or solvate thereof, is administered once per day for about 1 week, 2 weeks, 3 weeks, about 4 weeks, about 6 weeks, about 9 weeks, about 12 weeks, about 15 weeks, about 18 weeks, about 21 weeks, or about 26 weeks. In certain embodiments, the compound of Formula I or a pharmaceutically acceptable salt or solvate thereof is administered intermittently. In certain embodiments, the compound of Formula I or a pharmaceutically acceptable salt or solvate thereof is administered intermittently in the amount of from about 40 to 450 mg per day. In certain embodiments, the compound of Formula I or a pharmaceutically acceptable salt or solvate thereof is administered continuously. In certain embodiments, the compound of Formula I or a pharmaceutically acceptable salt or solvate thereof is administered continuously in the amount ranging from about 12 mg to 1000 mg per day. In certain embodiments, the compound of Formula I or a pharmaceutically acceptable salt or solvate thereof is administered continuously in the amount ranging from about 12 mg to 2000 mg per day, or from about 27 mg to 1000 mg per day. In certain embodiments, the compound of Formula I or a pharmaceutically acceptable salt or solvate thereof is administered continuously in the amount ranging from about 200 mg to 1000 mg per day. In certain embodiments, the compound of Formula I or a pharmaceutically acceptable salt or solvate thereof is administered continuously in the amount ranging from about 200 mg to 675 mg per day. In certain embodiments, the compound of Formula I or a pharmaceutically acceptable salt or solvate thereof is administered continuously in the amount ranging from about 200 mg to 450 mg per day. In certain embodiments, the compound of Formula I or a pharmaceutically acceptable salt or solvate thereof is administered continuously for 28 days. In certain embodiments, the compound of Formula I, or a pharmaceutically acceptable salt or solvate thereof, is administered continuously to a patient in the amount of about 12, about 18, about 20, about 25, about 27, about 30, about 35, about 40, about 45, about 50, about 55, about 60, about 90, about 135, about 150, about 200, about 300, about 450, or about 675 mg per day.

In certain embodiments, the compound of Formula I, or a pharmaceutically acceptable salt or solvate thereof, is cyclically administered to a patient. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

Consequently, In certain embodiments, the compound of Formula I, or a pharmaceutically acceptable salt or solvate thereof, is administered daily in a single or divided doses for one week, two weeks, three weeks, four weeks, five weeks, six weeks, eight weeks, ten weeks, fifteen weeks, or twenty weeks, followed by a rest period of about 1 day to about ten weeks. For example, the methods contemplate using cycling of one week, two weeks, three weeks, four weeks, five weeks, six weeks, eight weeks, ten weeks, fifteen weeks, or twenty weeks. In certain embodiments, the compound of Formula I, or a pharmaceutically acceptable salt or solvate thereof, is administered daily in a single or divided doses for one week, two weeks, three weeks, four weeks, five weeks, or six weeks with a rest period of 1, 3, 5, 7, 9, 12, 14, 16, 18, 20, 22, 24, 26, 28, 29, or 30 days. In some embodiments, the rest period is 14 days. In some embodiments, the rest period is 28 days. In certain embodiments, the rest period is a period that is sufficient for bone marrow recovery. The frequency, number and length of dosing cycles can be increased or decreased.

In certain embodiments, the methods provided herein comprise: i) administering to the mammal at a first daily dose of the compound of Formula I, or a pharmaceutically acceptable salt or solvate thereof; ii) resting for a period of at least one day where the compound of Formula I or a pharmaceutically acceptable salt or solvate thereof is not administered to the mammal; iii) administering a second dose of the compound to the mammal; and iv) repeating steps ii) to iii) a plurality of times. In certain embodiments, the first daily dose is from about 0.1 mg/kg to about 10 mg/kg. In certain embodiments, the second daily dose is from about 0.1 mg/kg to about 10 mg/kg. In certain embodiments, the first daily dose is higher than the second daily dose. In certain embodiments, the second daily dose is higher than the first daily dose.

In certain embodiments, the rest period is 2 days, 3 days, 5 days, 7 days, 10 days, 12 days, 13 days, 14 days, 15 days, 17 days, 21 days, or 28 days. In certain embodiments, the rest period is at least 2 days and steps ii) through iii) are repeated at least three times. In certain embodiments, the rest period is at least 2 days and steps ii) through iii) are repeated at least five times. In yet another embodiment, the rest period is at least 3 days and steps ii) through iii) are repeated at least three times. In yet another embodiment, the rest period is at least 3 days and steps ii) through iii) are repeated at least five times. In yet another embodiment, the rest period is at least 7 days and steps ii) through iii) are repeated at least three times. In yet another embodiment, the rest period is at least 7 days and steps ii) through iii) are repeated at least five times. In yet another embodiment, the rest period is at least 14 days and steps ii) through iii) are repeated at least three times. In yet another embodiment, the rest period is at least 14 days and steps ii) through iii) are repeated at least five times. In yet another embodiment, the rest period is at least 21 days and steps ii) through iii) are repeated at least three times. In yet another embodiment, the rest period is at least 21 days and steps ii) through iii) are repeated at least five times. In yet another embodiment, the rest period is at least 28 days and steps ii) through iii) are repeated at least three times. In still another embodiment, the rest period is at least 28 days and steps ii) through iii) are repeated at least five times.

It is understood that the duration of the treatment may vary with the age, weight, and condition of the patient being treated, and may be determined empirically using known testing protocols or according to the professional judgment of the person providing or supervising the treatment. In certain embodiments, the compound of Formula I, or a pharmaceutically acceptable salt or solvate thereof, is administered continuously for about 1 to about 52 weeks. In certain embodiments, the compound of Formula I, or a pharmaceutically acceptable salt or solvate thereof, is administered continuously for about 1, 2, 3, 4, 5, 6, 7, 8, 9, 10, 11, or 12 months. In certain embodiments, the compound of Formula I, or a pharmaceutically acceptable salt or solvate thereof, is administered continuously for about 14, about 28, about 42, about 84, or about 112 days.

In each embodiment provided herein, the method may further comprise a diagnostic step for determining the presence of a constitutively activating FLT3 mutant in a mammal.

In certain embodiments, the treatment of AML patients with the compound of Formula I, or a pharmaceutically acceptable salt or solvate thereof enables the patients to become eligible for allogeneic hematopoietic stem cell transplant (HSCT). In certain embodiments, the treatment with the compound of Formula I, or a pharmaceutically acceptable salt or solvate thereof is continued till the patient becomes eligible for allogeneic HSCT. The eligibility for allogeneic HSCT can be determined by one of skill in the art using appropriate techniques. In certain embodiments, the treatment with the compound of Formula I, or a pharmaceutically acceptable salt or solvate thereof is followed by an allogeneic HSCT.

The compound of Formula I or a pharmaceutically acceptable salt or solvate thereof can also be combined or used in combination with other therapeutic agents useful in the treatment and/or prevention of a disease described herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

The route of administration of the compound of Formula I or a pharmaceutically acceptable salt or solvate thereof is independent of the route of administration of a second therapy. In certain embodiments, the compound of Formula I or a pharmaceutically acceptable salt or solvate thereof is administered orally. In certain embodiments, the compound of Formula I is administered intravenously. Thus, in accordance with these embodiments, the compound of Formula I or a pharmaceutically acceptable salt or solvate thereof is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In certain embodiments, the compound of Formula I or a pharmaceutically acceptable salt or solvate thereof and a second therapy are administered by the same mode of administration, orally or by IV. In certain embodiments, the compound of Formula I or a pharmaceutically acceptable salt or solvate thereof is administered by one mode of administration, e.g., by IV, whereas the second agent (an anticancer agent) is administered by another mode of administration, e.g., orally.

In certain embodiments, each method provided herein may independently, further comprise the step of administering a second therapeutic agent. In certain embodiments, the second therapeutic agent is an anticancer agent. In certain embodiments, the anticancer agent is an antimetabolite, including, but not limited to, 5-fluoro uracil, methotrexate, cytarabine (also known as cytosine arabinoside or Ara-C), and HDAC (high dose cytarabine) and fludarabine. In yet another embodiment, the anticancer agent is an antimicrotubule agent, including, but not limited to, vinca alkaloids (e.g., vincristine and vinblastine) and taxanes (e.g., paclitaxel and docetaxel). In yet another embodiment, the anticancer agent is an alkylating agent, including, but not limited to, cyclophosphamide, melphalan, carmustine, and nitrosoureas (e.g., bischloroethylnitrosurea and hydroxyurea). In yet another embodiment, the anticancer agent is a platinum agent, including, but not limited to, cisplatin, carboplatin, oxaliplatin, satraplatin (JM-216), and CI-973. In yet another embodiment, the anticancer agent is an anthracycline, including, but not limited to, doxrubicin and daunorubicin. In yet another embodiment, the anticancer agent is an antitumor antibiotic, including, but not limited to, mitomycin, idarubicin, adriamycin, and daunomycin (also known as daunorubicin). In yet another embodiment, the anticancer agent is a topoisomerase inhibitor, e.g., etoposide and camptothecins. In yet another embodiment, the anticancer agent is selected from the group consisting of adriamycin, busulfan, cytarabine, cyclophosphamide, dexamethasone, fludarabine, fluorouracil, hydroxyurea, interferons, oblimersen, platinum derivatives, taxol, topotecan, and vincristine.

In certain embodiments, the anticancer agent is a Bcr-Abl kinase inhibitor. In certain embodiments, the Bcr-Abl kinase inhibitor is selected from the group consisting of imatinib, BMS354825 (dasatinib), AMN107 (nilotinib), AP23464, AZD0530, CGP76030, ON012380, INN-0406 (NS-187), SKI-606 (bosutinib), VX-680, and pyrrolo[2,3-d]pyrimidines including PD166326, PD173955 and PD180970. In certain embodiments, the Bcr-Abl kinase inhibitor is imatinib. In yet another embodiment, the Bcr-Abl kinase inhibitor is dasatinib. In yet another embodiment, the Bcr-Abl kinase inhibitor is nilotinib. In yet another embodiment, the Bcr-Abl kinase inhibitor is AP23464. In yet another embodiment, the Bcr-Abl kinase inhibitor is AZD0530. In yet another embodiment, the Bcr-Abl kinase inhibitor is CGP76030. In yet another embodiment, the Bcr-Abl kinase inhibitor is SKI-606. In yet another embodiment, the Bcr-Abl kinase inhibitor is ON012380. In yet another embodiment, the Bcr-Abl kinase inhibitor is INN-0406 (NS-187). In yet another embodiment, the Bcr-Abl kinase inhibitor is a pyrrolo[2,3-d]pyrimidine. In certain embodiments, the Bcr-Abl kinase inhibitor is VX-680. In certain embodiments, the Bcr-Abl kinase inhibitor is PD166326. In yet another embodiment, the Bcr-Abl kinase inhibitor is PD173955. In still another embodiment, the Bcr-Abl kinase inhibitor is PD180970.

In still another embodiment, the anticancer agent is a FLT3 kinase inhibitor. In certain embodiments, the FLT3 kinase inhibitor is selected from the group consisting of PKC 412, MLN 518, CEP-701, UCN-01, UCN-02, CT 53518, CT-53608, CT-52923, D-64406, D-65476, AGL-2033, AG1295, AG1296, KN-1022, KW-2449, SU5416, SU5614, SU11248, L-00021649, VX-322, VX-398, VX-680, AP-24534, AST-487, sorafenib and CHIR-258. In certain embodiments, the FLT3 kinase inhibitor is PKC 412. In yet another embodiment, the FLT3 kinase inhibitor is MLN 518. In yet another embodiment, the FLT3 kinase inhibitor is CEP-701. In yet another embodiment, the FLT3 kinase inhibitor is CT 53518. In yet another embodiment, the FLT3 kinase inhibitor is CT-53608. In yet another embodiment, the FLT3 kinase inhibitor is CT-52923. In yet another embodiment, the FLT3 kinase inhibitor is D-64406. In yet another embodiment, the FLT3 kinase inhibitor is D-65476. In yet another embodiment, the FLT3 kinase inhibitor is AGL-2033. In yet another embodiment, the FLT3 kinase inhibitor is AG1295. In yet another embodiment, the FLT3 kinase inhibitor is AG1296. In yet another embodiment, the FLT3 kinase inhibitor is KN-1022. In yet another embodiment, the FLT3 kinase inhibitor is KN-1022. In yet another embodiment, the FLT3 kinase inhibitor is SU5416. In yet another embodiment, the FLT3 kinase inhibitor is KW2449. In yet another embodiment, the FLT3 kinase inhibitor is SU5614. In yet another embodiment, the FLT3 kinase inhibitor is SU11248. In yet another embodiment, the FLT3 kinase inhibitor is L-00021649. In yet another embodiment, the FLT3 kinase inhibitor is VX-322. In yet another embodiment, the FLT3 kinase inhibitor is VX-398. In yet another embodiment, the FLT3 kinase inhibitor is VX-680. In yet another embodiment, the FLT3 kinase inhibitor is sorafenib. In yet another embodiment, the FLT3 kinase inhibitor is AP-24534. In yet another embodiment, the FLT3 kinase inhibitor is AST-487. In still another embodiment, the FLT3 kinase inhibitor is CHIR-258.

Other therapies or anticancer agents that may be used in combination with the compound of Formula I or a pharmaceutically acceptable salt or solvate thereof include surgery, radiotherapy (e.g., gamma-radiation, neutron beam radiotherapy, electron beam radiotherapy, proton therapy, brachytherapy, and systemic radioactive isotopes), endocrine therapy, biologic response modifiers (e.g., interferons, interleukins, and tumor necrosis factor (TNF)), hyperthermia and cryotherapy, agents to attenuate any adverse effects (e.g., antiemetics), and other approved chemotherapeutic drugs, including, but not limited to, alkylating drugs (mechlorethamine, chlorambucil, cyclophosphamide, melphalan, and ifosfamide), antimetabolites (cytarabine (also known as cytosine arabinoside or Ara-C), HDAC (high dose cytarabine), and methotrexate), purine antagonists and pyrimidine antagonists (6-mercaptopurine, 5-fluorouracil, cytarbine, and gemcitabine), spindle poisons (vinblastine, vincristine, vinorelbine, and paclitaxel), podophyllotoxins (etoposide, irinotecan, and topotecan), antibiotics (daunorubicin, doxorubicin, bleomycin, and mitomycin), nitrosoureas (carmustine and lomustine), inorganic ions (cisplatin and carboplatin), enzymes (asparaginase), and hormones (tamoxifen, leuprolide, flutamide, and megestrol), imatinib, adriamycin, dexamethasone, and cyclophosphamide. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

EXAMPLES

Example 1

Phase I clinical trial

This study was the first human clinical trial of the compound of Formula I or a pharmaceutically acceptable salt or solvate thereof in humans having relapsed or refractory acute myeloid leukemia. The study was open labeled and designed to determine the safety, tolerability, dose limiting toxicity (DLT), pharmacokinetics and pharmacodynamics of escalating doses.

The study included adult patients with relapsed or refractory AML, or unsuitable for induction chemotherapy. Demographics and baseline characteristics were as follows: median age was 60 years, with a range of 23-86 years. Sixty percent of the patients were male. Approximately 73% of the patients had a baseline ECOG performance status of 0 or 1 and the median number of prior therapies was 4 with a range of 0 to 9. Eleven (15%) patients had prior allogeneic hematopoietic stem cell transplant (HSCT) and 13 (17%) patients had secondary AML with antecedent MDS or MDS/MPD. A total of 20 patients had FLT3 mutations (17 ITD and 3 D835), 43 were wild-type, and 13 were undetermined.

Drug Administration

The compound of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt was administered at 12, 18, 27, 60, 90, 135, 200, 300 and 450 mg for 14 days followed by a 14 day rest period (1 cycle). Patients with clinical benefit were allowed to continue for additional cycles at the discretion of the investigator. The protocol was subsequently amended to allow for continuous dosing of the compound starting at 200 mg on Day 1. In addition to patients included in the 200 mg (17 patients) and 300 mg (8 patients) continuous dosing cohort, there were at least 8 patients who, at the investigators discretion and per protocol, received continuous dosing after cycle 1 of intermittent dosing ranging from 19-187 days.

Safety

Overall, treatment with N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt was well tolerated, and the majority of adverse events observed in the study were those associated with the underlying disease and not considered related to the treatment with the compound of formula I. The frequency and type of adverse events were similar across the dose groups. In addition, the safety profile was similar between patients receiving continuous dosing and those on the intermittent schedule. These included general disorders (e.g., pyrexia and fatigue), gastrointestinal disorders (e.g., nausea, diarrhea and vomiting) and hematologic disorders (eg, anemia, neutropenia and thrombocytopenia). The majority of the treatment-related adverse events were CTC Grade 1 and 2 and not considered serious.

Bone marrow hypocellularity was a target organ toxicity in the animal studies however, this toxicity is difficult to assess in the ongoing AML Phase 1/2 study since tumor related myelosuppression is a prevalent AML-related disease manifestation and is present in almost all AML patients enrolled in the ongoing clinical study. In addition, evaluation of clinical chemistry biomarkers (eg, BUN, creatinine, ALT, AST, ALP, and bilirubin) for the other target organ toxicities identified in animal toxicology studies suggest there are no liver or kidney abnormalities occurring in the ongoing clinical study as drug-related serious adverse events.

Serious Adverse Events

Out of the 76 patients treated with the compound in this study, 38 patients (50%) reported a total of 94 serious adverse events (SAEs) (defined as CTC Grade 3 or greater). The majority of the SAEs were considered by the investigator to be not related to study treatment. Only 6 patients (7.9%) reported SAEs that were initially considered to be related to treatment with the compound. These included one patient with lung infection, one patient with vomiting and one patient with nausea, anorexia, and upper abdominal pain. The investigator subsequently revised the event of anorexia for the patient to non-serious. In addition, three patients were noted by the site investigators using local ECG analysis to have reported Grade 3 QTc prolongation of >500 ms which was considered to be a dose-limiting toxicity for the study according to the protocol.

Cardiac Safety

Based on the site reported dose-limiting toxicity of Grade 3 QTc prolongation, a detailed evaluation of the cardiac safety of the compound was conducted. As defined in the protocol, a single 12-lead electrocardiogram (ECG) had been performed using standardized equipment at the site at Visits 1 (screen), 2 (Baseline—at Hours 0, 2, and 4), 4 (Day 8 at Hours 0 and 4), and depending on the version of the protocol active at the time of assessment for each patient, 6 (Day 14 or 15), 7 (Day 21 or 22), 8 (Day 28 or 29), 9 (Day 36), 10 (Day 43), 11 (Day 50), 12 (Day 57) and at the end of the study or early termination. ECG assessments and interpretations initially were performed by the site's cardiologist or other qualified site personnel. To improve upon the accuracy of these locally-analyzed data, a central digitized blinded analysis of all ECGs collected to date was undertaken by a core ECG laboratory (EResearchTechnology in Philadelphia, Pa.). Due to some issues with readability, 72 patients (out of 76 patients enrolled in the study) were included in this analysis. The data demonstrated a clear dose-related and marked QTc change at the ≥200 mg dose level. However, caution must be exercised in viewing these results due to the small sample sizes and lack of intense ECG sampling. The phase I study was not designed to define the ECG effects of the compound, which will be more closely monitored in the phase II study.

Deaths

To date, a total of 12 patients have died during the study. All deaths were associated with the disease and/or pre-existing comorbidities and not related to treatment with the compound. Therefore, there is no 30-day treatment-related mortality reported to date. This is in contrast to other AML therapies including standard induction chemotherapy which report 30-day treatment-related mortalities of up to 30% of more than 500 ms which was considered to be the dose-limiting toxicity for the study per protocol.

Efficacy

Preliminary response data was evaluated in all 76 patients treated with the compound. Four of the patients on the 200 mg CD cohort and 1 patient on the 300 mg CD cohort were considered non-evaluable due to the limited duration of their treatment to date.

The overall response (CR+PR) observed in all patients treated at dosed from 12 mg-450 mg was 32% (24/76) of the compound. Responses were defined per modified Cheson criteria. Ten patients achieved a complete remission (CR) defined as a decrease of ≤5% blast in bone marrow: 2 complete hemologic recovery, 4 with incomplete platelet recovery (CRp) and 4 with incomplete platelet and neutrophil recovery (CRi). One of these patients also had complete resolution of leukemia cutis. Fourteen patients had partial remissions (PR) defined as a decrease of ≥50% blasts to levels of 5%-25% in the bone marrow but with incomplete peripheral recovery of neutrophils and platelets. Most of the patients report a bone marrow responses (15/22, 68%) within the first 29 days of treatment (defined as Cycle 1). Of the remaining 7 patients, 4 patients reported a response within 57 days (Cycle 2), 3 patients thereafter. Median duration of remission was 14.1 weeks (range, 4 to 61+ weeks). In addition, most patients had a peripheral blast reduction defined as >25% peripheral blasts at baseline with >50% decrease post-treatment to 0-25%.

The response in the population the FLT3-ITD mutation was higher with an overall response rate of 65% (11/17) including 6 PR, 3 CRi, 1 CRp and 1 CR. Five of the 7 non-responding patients with FLT3-ITD mutations did not have a repeat bone marrow assessment, and therefore, could not be assessed for bone marrow response.

All of these patients had initial rapid clearing of peripheral blasts with intermittent dosing and subsequently progressed or had disease-related mortality. The FLT3-ITD patient population had very aggressive disease and was generally heavily pretreated with a median of 4 prior treatment regimens (range, 1 to 8) including 5 patients who were previously treated with FLT3 inhibitors.

All FLT3-ITD patients treated with 200 mg CD responded to treatment with an overall response rate (CR+CRp+CRi+PR) of 100% (5/5) including 1 CR, 1 CRp, 1CRi and 2 PRs. The duration of response of overall CR was confounded due to dose interruption. Two patients, who had relapsed disease, subsequently responded with a CRp and CRi with the treatment with the compound and were taken off study to go to bone marrow transplant. One patient had dosing interrupted due to a disrupted drug supply. In addition, both patients reporting a PR were heavily pretreated and one was previously treated with a FLT3 inhibiting agent (sorafenib). A total of 2 of the 5 responding patients in this cohort were previously treated with sorafenib. Two additional patients in the 200 mg CD cohort reported CR and CRi but had undetermined genotype due to a lack of sufficient peripheral blasts for testing.

Pharmacokinetics

Figure 2A:
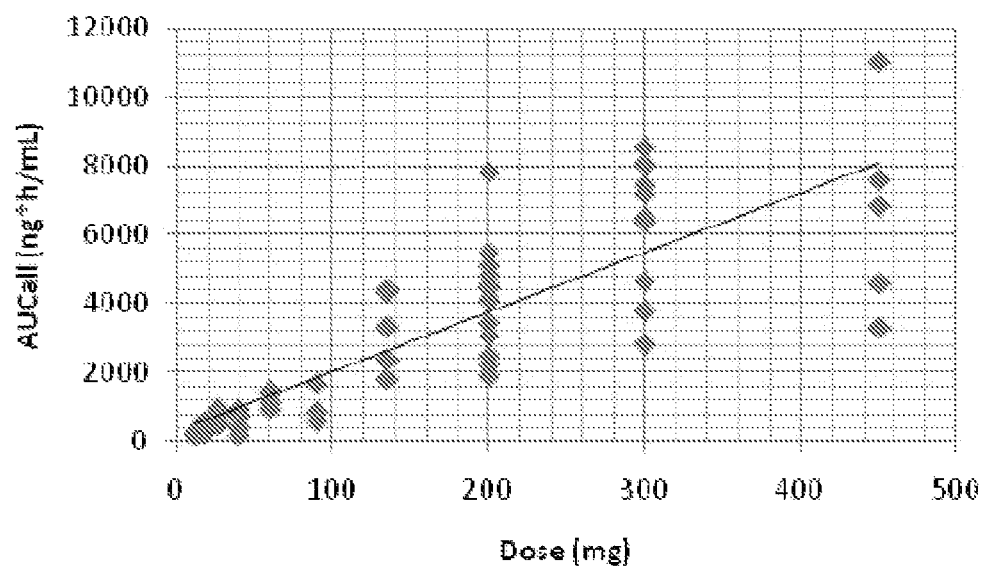
FIG. 2A depicts the dose response of the exposure (AUC) in humans to N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt at day 1.
Figure 2B:
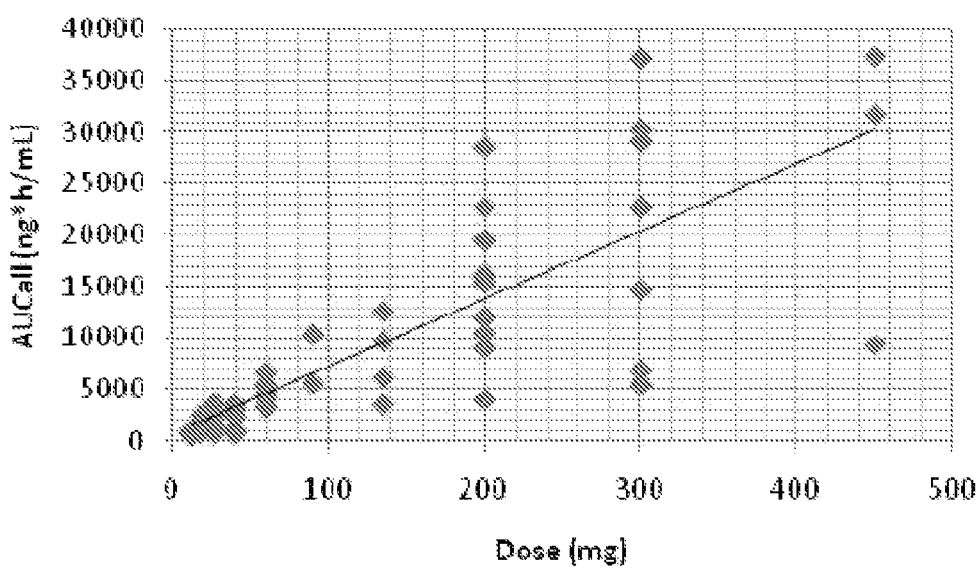
FIG. 2B depicts the dose response of the exposure (AUC) in humans to N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt at day 8.

Plasma samples were collected at pre-dose, 0.25, 0.5, 1, 2, 4, 6, 9, 24 hr on Days 1 and 8 to evaluate the pharmacokinetics of N-(5-tert-butyl-isoxazol-3-yl)-N'-{4-[7-(2-morpholin-4-yl-ethoxy)imidazo[2,1-b][1,3]benzothiazol-2-yl] phenyl}urea di-hydrochloride salt. In addition, plasma samples were collected on day 15 (~24 hrs post final dose) to evaluate steady-state trough levels. Bioanalysis of the compound was initially conducted at Consolidated Laboratory Services (CLS), Van Nuys, Calif. A similar pharmacokinetic profile was observed in all patients evaluated (n=72), with levels of the compound rising rapidly during the first day of dosing (FIG. 1). The compound is orally bioavailable with a long effective half-life, estimated to be approximately 1.5 days. In addition, the compound exhibits minimal peak and trough variation of plasma levels with once daily dosing. The steady-state plasma exposure is achieved by Day 8, sustained between dose intervals and increased in a dose proportional manner from 12 mg to 450 mg daily (FIGS. 2A and 2B). The coefficient of variation (CV %) for AUC0-24 at steady-state is modest at the lowest dose of 12 mg (33%) and high for the 450 mg cohort (82%). While the variability tended to be higher at higher doses, there was not a clear relationship between variability and either dose or high-life.

A pharmacologically active metabolite, compound of formula II, was identified in both preclinical species and human plasma and urine samples.

Formula II

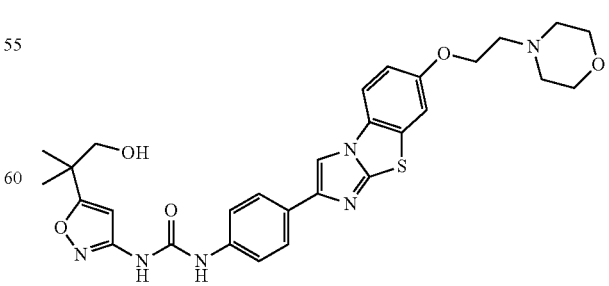

N-(5-tert-Butyl-isoxazol-3-yl)-N'-{4-[7-(2-morpholin-4-yl-ethoxy)imidazo[2,1-b][1,3]benzothiazol-2-yl]

phenyl}urea di-hydrochloride salt and II were subsequently analyzed in human plasma from a subset of patients (n=60) dosed with N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt. This analysis was conducted at MicroConstants, San Diego, Calif. The analysis revealed a ratio of the compounds of formula II/I as high as 3.14 in one patient, with an average steady state ratio of 0.4. Patients dosed at 200 mg the compound of formula I achieve steady-state plasma levels for the compounds of formula I and II of ~1000 ng/mL and ~300 ng/mL, respectively. These data from MicroConstants indicate that the compound of formula I has a long terminal $T_{1/2}$ at 1.3±0.4 days on Day 1.

Figure 3A:
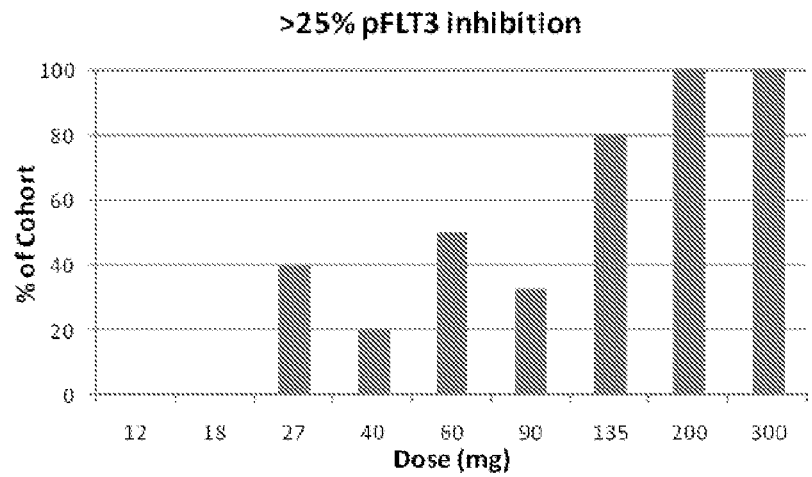
FIG. 3A shows percentage of patients demonstrating at least 25% pFLT3 inhibition by N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt in an Ex Vivo Plasma Inhibitory Assay.
Figure 3B:
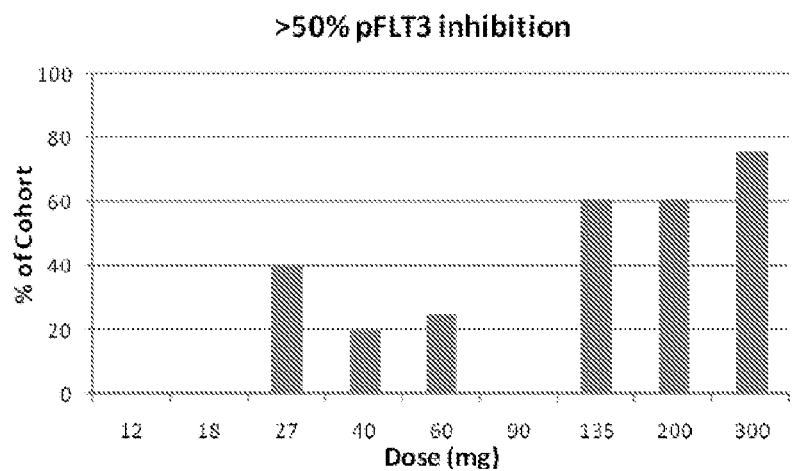
FIG. 3B shows percentage of patients demonstrating at least 50% pFLT3 inhibition by N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt in an Ex Vivo Plasma Inhibitory Assay.
Figure 3C:
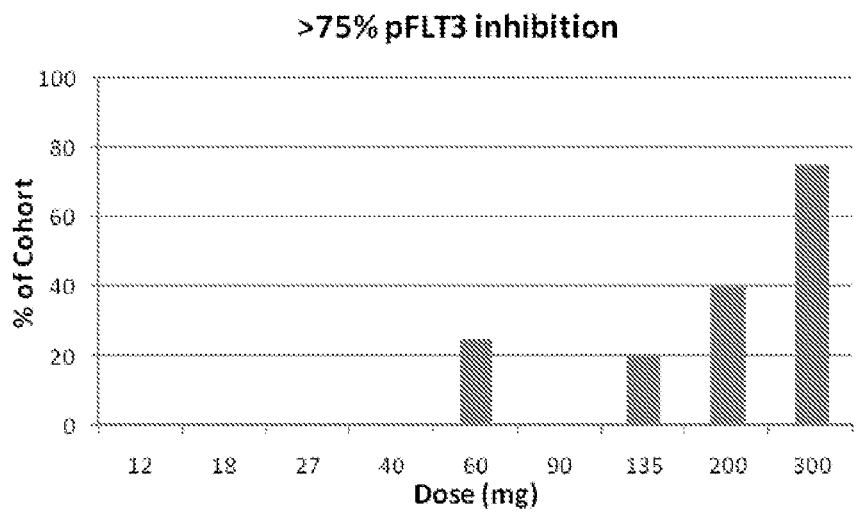
FIG. 3C shows percentage of patients demonstrating at least 75% pFLT3 inhibition by N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt in an Ex Vivo Plasma Inhibitory Assay.

Pharmacodynamic Effect of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt Patient blood samples were drawn pre-dose and at regular intervals post-dose to determine the level of pFLT3 and other downstream markers of target inhibition in circulating blast cells. To date, pFLT3 levels have been evaluated in 41 patient samples at pre- and 24 hr post-dose time-points. The preliminary results indicate that the percentage of patients demonstrating at least 25% pFLT3 inhibition increased dramatically with increased dose of the compound (FIG. 3A). FIGS. 3B and 3C show the percentage of patients demonstrating at least 50% and at least 75% pFLT3 inhibition. There was also a dose dependent increase in the degree of pFLT3 inhibition in response to the compound. In the 200 and 300 mg dose cohort, 100% of the patients achieved >25% reduction in pFLT3 activity. In addition, several patients in these two cohorts responded with a greater that 85% inhibition of pFLT3.

Figure 4:
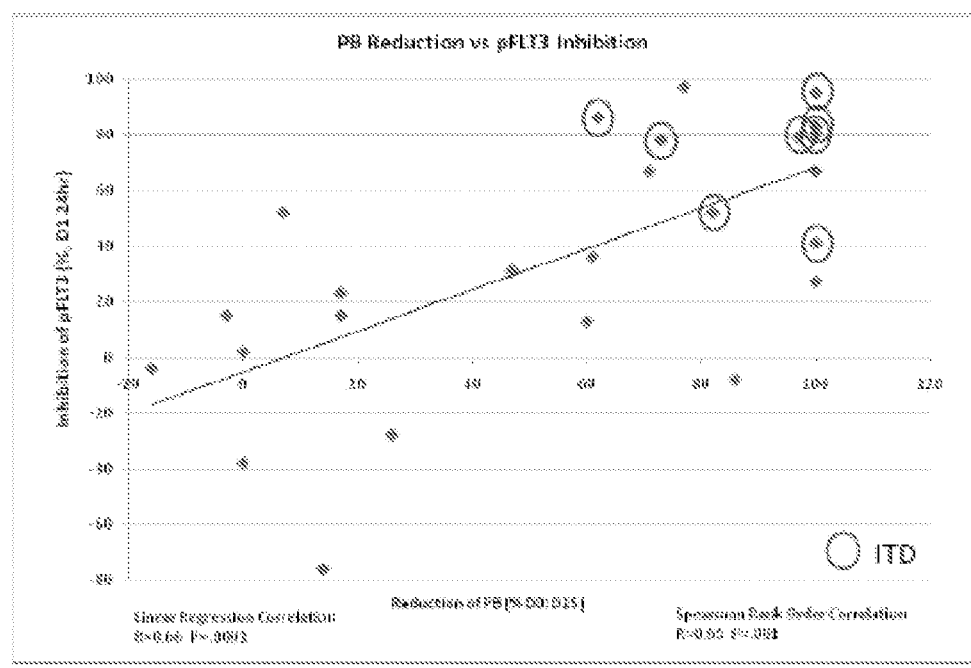
FIG. 4 demonstrates higher level of correlation of the pFLT3 inhibition with reduction in peripheral blast count after 14 days of treatment with N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt.

It was not always possible to correlate bone marrow response with inhibition of pFLT3 due to the lack of follow-up bone marrow samples for some patients. However, extensive follow-up information on peripheral blast count was available for all patients. A total of 25 out of 41 patients with an assessment of pFLT3, had an evaluation on day 15. As shown in FIG. 4, on day 15 of the study, after 14 days of treatment with the compound, there was a high level of correlation of the pFLT3 inhibition with reduction in peripheral blast count (R=0.65, p≤0.001). The magnitude of observed reduction in peripheral blasts increased with increased inhibition of pFLT3. All 8 patients harboring the FLT3-ITD mutation that were the FLT3-ITD mutation evaluated had large reductions in both pFLT3 and peripheral blasts in response to treatment with the compound (FIG. 4).

A subset of 17 patients has also been evaluated for the effect of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt on pSTAT5. STAT5 is a downstream signaling pathway activated by FLT3 following binding of FLT3 ligand leading to receptor dimerization, increased kinase activity and activation of downstream signaling pathways including STAT5. Although the data on pSTAT5 are very preliminary, the dose-dependent effect is consistent with that observed with pFLT3.

Example 2

Preparation of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt capsules 75 mg 75 mg of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt was suspended in a waxy matrix of lauroyl polyoxylglycerides (GELUCIRE® 44/14, Gattefosse). To produce approximately 4,000 Capsules 75 mg, a mixture of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt (300 g) and GELUCIRE® 44/14 (1,900 g) in a suitably sized jacketed vessel was stirred at approximately 70° C. until molten. The molten mixture was slowly charged into the vortex of a container and mixed until a homogeneous suspension was obtained. The suspension was maintained at a blend temperature of 70° C. and deaerated under vacuum. With gentle mixing to avoid incorporation of air, the suspension was allowed to cool to a temperature of 50° C. The suspension was then charged into a heated hopper attached to a CAPSUGEL® CSF1200 or similar encapsulation machine. Each capsule was filled with the suspension to an average weight of 550 mg. The finished capsules were allowed to cool prior to packaging into appropriate containers.

Example 3

Preparation of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt powder in bottle 350 mg The composition comprises 350 mg of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt and no additional excipients. To produce 2,000 bottles, N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt (350 mg) was weighed using a calibrated balance into a 100 mL bottle. Each bottle was sealed with a rubber stopper and a flip off seal.

Powder in Bottle 350 was reconstituted prior to use with a 5% solution of hydroxypropyl-β-cyclodextrin to a concentration of 5 mg/mL of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt. The reconstituted N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt was dosed as an oral solution.

Example 4

Preparation of N-(5-tert-butyl-isoxazol-3-yl)-N'-{4-[7-(2-morpholin-4-yl-ethoxy)imidazo[2,1-b][1,3]-benzothiazol-2-yl]phenyl}urea di-hydrochloride salt lyophilized powder in bottle 75 mg The composition comprises of 75 mg of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt and 75 mg of hydroxypropyl-β-cyclodexin. To produce 4,000 bottles, a solution of hydroxypropyl-β-cyclodexin (6 L) was prepared by dissolving hydroxypropyl-β-cyclodexin (3 kg) in a suitable container. With continued agitation, N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt (300 g) was added to the solution, and mixed until dissolved, if necessary, with heat. The solution was filtered before filling. Each 30 mL bottle was filled with 15 mL of the solution. After the filling, the solution in each bottle was flash frozen and lyophilized. The bottle was then sealed tightly.

Prior to dosing, Lyophilized Powder in Bottle 75 was reconstituted by adding 15 mL of water to the bottle and swirling the bottle gently for one minute until powder was dissolved. The reconstituted N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt was dosed as an oral solution.

Example 5

Additional Formulations

Additional formulations that were prepared are summarized in Table 11, along with methods of their preparation. Certain formulations in Table 11 were studied in vivo.

TABLE 11

| Formulation | Preparation |
| --- | --- |
| 3 mg/mL of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt in a 22% HPBCD solution | a. Prepare a 22% HPBCD solution.<br>b. Dissolve 3 mg of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt in 1 mL of the HPBCD solution |
| 1, 3, 10 mg/mL of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt in a 22% HPBCD Solution | a. Prepare a 22% HPBCD solution.<br>b. Dissolve 1, 3, or 10 mg of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt in 1 mL of the HPBCD solution |
| N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt in PEG 400 and Water (3:1) | a. Add PEG400 to N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt (75% of total volume required for 1 mg/mL) and vortex or sonicate until in solution.<br>b. Slowly add water while swirling (25% of total volume required for 1 mg/mL) and vortex or sonicate to mix well |
| 3 mg/mL of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt in a 5% HPBCD Solution | a. Prepare a 5% HPBCD solution.<br>b. Dissolve 30 mg of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt in 10 mL of the HPBCD solution |
| N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt (75 mg)<br>Mannitol (282 mg)<br>EXPLOTAB ® (22.8 mg) | a. Weigh out individual ingredients<br>b. Blend and fill capsules. |
| N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt (25 mg)<br>Mannitol (332 mg)<br>EXPLOTAB ® (22.8 mg) | a. Weigh out individual ingredients<br>b. Blend and fill capsules. |
| N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt (75 mg)<br>Mannitol (206 mg)<br>EXPLOTAB ® (22.8 mg)<br>Citric Acid (76 mg) | a. Weigh out individual ingredients<br>b. Blend and fill capsules. |
| N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt (25 mg)<br>Mannitol (309 mg)<br>EXPLOTAB ® (22.8 mg)<br>Citric Acid (25 mg) | a. Weigh out individual ingredients<br>b. Blend and fill capsules. |
| 5 mg/mL of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt in 5% HPBCD | a. Prepare a 5% HPBCD solution.<br>b. Dissolve 5 mg of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt in 1 mL of the HPBCD solution. |
| Hot Melt Granulation<br>PEG6000 (31%)<br>Mannitol (43.3%)<br>EXPLOTAB ® (12%)<br>N-(5-tert-butyl-isoxazol-3-yl)-N'-{4- | 1. Melt PEG, mannitol, and the compound of Formula I.<br>2. Dry, screen, and then blend with remaining mannitol and EXPLOTAB ®. |

TABLE 11-continued

| Formulation | Preparation |
| --- | --- |
| [7-(2-morpholin-4-yl-ethoxy)imidazo[2,1-b][1,3]benzothiazol-2-yl]phenyl}urea di-hydrochloride salt (50 mg) Hot Melt Granulation PEG6000 (18.8%) Mannitol (61.2%) EXPLOTAB ® (12%) N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt (30 mg) | 1. Melt PEG, mannitol, and the compound of Formula I. 2. Dry, screen, and then blend with remaining mannitol and EXPLOTAB ®. |
| Wet Granulation N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt (75 mg) Mannitol (226 mg) PVP (14 mg) EXPLOTAB ® (35 mg) | 1. Granulate PVP solution, EXPLOTAB ®, mannitol, and the compound of Formula I. 2. Dry, screen, and blend with remaining EXPLOTAB ® and mannitol. |
| Wet Granulation N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt (25 mg) Mannitol (276 mg) PVP (14 mg) EXPLOTAB ® (35 mg) | 1. Granulate PVP solution, EXPLOTAB ®, mannitol, and the compound of Formula I. 2. Dry, screen, and blend with remaining EXPLOTAB ® and mannitol. |
| Micronized the compound of Formula I N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt (75 mg) Mannitol (282 mg) EXPLOTAB ® (22.8 mg) | 1. Prepare micronized compound of Formula I using Jet-mill. 2. Weigh out individual ingredients, blend, and fill capsule. |
| Micronized the compound of Formula I N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt (25 mg) Mannitol (332 mg) EXPLOTAB ® (22.8 mg) | 1. Prepare micronized compound of Formula I using Jet-mill 2. Weigh out individual ingredients, blend, and fill capsule. |
| Liquid Fill N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt (50 mg) GELUCIRE ® 44/14 (470 mg) | 1. Heat GELUCIRE ® until liquid. 2. Disperse N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt into GELUCIRE ®. 3. While warm, dispense the suspension into capsules. |
| 3 mg/mL of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt in a 5% HPBCD Solution | 1. Prepare a 5% HPBCD solution. 2. Dissolve 30 mg of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt in 10 mL of the solution |
| 18 mg/mL of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt in GELUCIRE ® | 1. Heat GELUCIRE ® until liquid. 2. Disperse N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt into GELUCIRE ®. 3. While warm, dispense the suspension into capsules. |
| 75% GELUCIRE ® 44/14 25% PEG6000 | 1. Heat GELUCIRE ® and PEG6000 separately until liquid. 2. Combine the two and then dispense N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt into mixture. 3. While warm, dispense the suspension into capsules. |

TABLE 11-continued

| Formulation | Preparation |
|---|---|
| N-(5-tert-Butyl-isoxazol-3-yl)-N'-{4-[7-(2-morpholin-4-yl-ethoxy)imidazo[2,1-b][1,3]benzothiazol-2-yl]phenyl}urea di-hydrochloride salt (70 mg)<br>Mannitol (275.5 mg)<br>EXPLOTAB ® (22.8 mg)<br>PLURONIC ® F68 (11.4 mg) | 1. Blend N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt with powder components by geometric dilution.<br>2. Dispense blended powder into capsules |
| N-(5-tert-Butyl-isoxazol-3-yl)-N'-{4-[7-(2-morpholin-4-yl-ethoxy)imidazo[2,1-b][1,3]benzothiazol-2-yl]phenyl}urea di-hydrochloride salt (164 mg/mL) in GELUCIRE ®:<br>N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt (100 mg)<br>GELUCIRE ® 44/14 (0.7 mL)<br>GELUCIRE ® Hot Melt | 1. Heat GELUCIRE ® until liquid.<br>2. Disperse N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt into GELUCIRE ®.<br>3. While warm, dispense the suspension into capsules |
| N-(5-tert-Butyl-isoxazol-3-yl)-N'-{4-[7-(2-morpholin-4-yl-ethoxy)imidazo[2,1-b][1,3]benzothiazol-2-yl]phenyl}urea di-hydrochloride salt (60 mg)<br>GELUCIRE ® 44/14 (37.5 mg)<br>PEG 6000 (112.5 mg)<br>Silicone Dioxide (10 mg)<br>Mannitol (117.5 mg)<br>EXPLOTAB ® (37.5 mg) | 1. Mix GELUCIRE ® with liquid N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt to form a suspension.<br>2. Melt PEG 6000 and mannitol together and then mix with the suspension.<br>3. Dry, screen, and blend with remaining mannitol and EXPLOTAB ®. |
| N-(5-tert-Butyl-isoxazol-3-yl)-N'-{4-[7-(2-morpholin-4-yl-ethoxy)imidazo[2,1-b][1,3]benzothiazol-2-yl]phenyl}urea di-hydrochloride salt (150 mg/mL) in GELUCIRE ®:<br>N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt (63 mg)<br>GELUCIRE ® 44/14 (0.5 mL) | 1. Heat GELUCIRE ® until liquid.<br>2. Disperse N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt into GELUCIRE ®.<br>3. While warm, dispense the suspension into capsules |
| N-(5-tert-Butyl-isoxazol-3-yl)-N'-{4-[7-(2-morpholin-4-yl-ethoxy)imidazo[2,1-b][1,3]benzothiazol-2-yl]phenyl}urea di-hydrochloride salt (125 mg/mL) in GELUCIRE ®:<br>N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt (55 mg)<br>GELUCIRE ® 44/14 (0.5 mL) | 1. Heat GELUCIRE ® until liquid.<br>2. Disperse N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt into GELUCIRE ®.<br>3. While warm, dispense the suspension into capsules |
| N-(5-tert-Butyl-isoxazol-3-yl)-N'-{4-[7-(2-morpholin-4-yl-ethoxy)imidazo[2,1-b][1,3]benzothiazol-2-yl]phenyl}urea di-hydrochloride salt (70 mg)<br>HPBCD (140 mg)<br>Mannitol (119 mg)<br>EXPLOTAB ® (21 mg)<br>Lyophilized material (110 mg) | 1. Mix N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt and HPBCD.<br>2. Lyophilize |
| N-(5-tert-Butyl-isoxazol-3-yl)-N'-{4-[7-(2-morpholin-4-yl-ethoxy)imidazo[2,1-b][1,3]benzothiazol-2-yl]phenyl}urea di-hydrochloride salt (10 mg)<br>HPBCD (100 mg)<br>Material reconstituted to 5 mg/ml with water<br>Lyophilized material (60 mg) | 1. Prepare a 5% HPBCD solution.<br>2. Dissolve 5 mg of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt in 1 mL of 5% HPBCD solution.<br>3. Freeze the solution and lyophilize over night. |
| N-(5-tert-Butyl-isoxazol-3-yl)-N'-{4-[7-(2-morpholin-4-yl-ethoxy)imidazo[2,1-b][1,3]benzothiazol-2-yl]phenyl}urea di-hydrochloride salt (10 mg) | 1. Prepare a 5% HPBCD solution.<br>2. Dissolve 10 mg of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt in 1 mL of 5% HPBCD solution. |

TABLE 11-continued

| Formulation | Preparation |
| --- | --- |
| HPBCD (50 mg)<br>Material reconstituted to 5 mg/ml<br>with water | 3. Freeze the solution and lyophilize over night. |

Example 6

1.1 g Batch Spray-Dried Composition 40 mg of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt was dissolved for each mL of 40% HPBCD solution by stirring until complete dissolution, for a total of 100 mg compound dissolved in a total of 2.5 mL 40% HPBCD solution. The solution was fed through a spray dryer (Buchi Mini Spray Drier B290) at 80° C.±5° C. to produce a 1.1 g batch of spray-dried material. Solids were collected and weighed into appropriate dosing containers.

The spray-dried composition in the container was reconstituted prior to use to 5 mg/mL with water. The reconstituted compound of Formula I is dosed as an oral solution.

Example 7

2.2 g Batch Spray-Dried Composition 40 mg of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt was dissolved for each mL of 40% HPBCD solution by stirring until complete dissolution, for a total of 200 mg compound dissolved in a total of 5 mL 40% HPBCD solution. The solution was fed through a spray dryer (Buchi Mini Spray Drier B290) at 80° C.±5° C. to produce a 2.2 g batch of spray-dried material. Solids were collected and weighed into appropriate dosing containers.

The spray dried composition in the container was reconstituted prior to use to 5 mg/mL with water. The reconstituted compound of Formula I is dosed as an oral solution.

Example 8

Batch Production of Spray Dried Composition 10 kg HPBCD and 15 kg deionized water were charged in a glass reactor and stirred till complete dissolution. No suspended solids were observed at the end of stirring period. 1 kg of N-(5-tert-butyl-isoxazol-3-yl)-N'-{4-[7-(2-morpholin-4-yl-ethoxy)imidazo[2,1-b][1,3]benzothiazol-2-yl]phenyl}urea di-hydrochloride salt was added to the reactor followed by 3 kg deionized water. The mixture was stirred till complete dissolution at temperature between 15° C. to 25° C. Additional 10 kg deionized water was added. The solution was fed through a spray dryer (Niro Mobile Minor 2000 Spray Drier) at 80° C.±5° C. Solids were collected.

The spray-dried composition is reconstituted prior to use to 5 mg/mL with water. The reconstituted compound of Formula I is dosed as an oral solution.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

The example set forth above is provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A spray-dried pharmaceutical composition comprising a compound of Formula I,

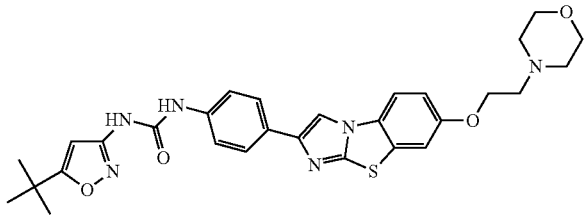 [SMILES: CC(C)(C)c1cc(NC(=O)Nc2ccc(-c3cn4c(n3)sc3cc(OCCN5CCOCC5)ccc34)cc2)no1]

or a pharmaceutically acceptable salt or solvate thereof, and hydroxypropyl-β-cyclodextrin.

2. The pharmaceutical composition of claim 1, wherein the pharmaceutically acceptable salt is a dihydrochloride salt.

3. The pharmaceutical composition of claim 1, wherein the solvate is a methanol solvate.

4. The pharmaceutical composition of claim 1 comprising the pharmaceutically acceptable salt of compound of Formula I and hydroxypropyl-β-cyclodextrin in a ratio of about 1:10 based on weight.

5. The pharmaceutical composition of claim 1, wherein the composition is formulated for single dose administration.

6. The pharmaceutical composition of claim 1, wherein the composition is formulated for oral administration.

* * * * *